United States Patent
Dinsmoor et al.

(10) Patent No.: US 11,707,626 B2
(45) Date of Patent: Jul. 25, 2023

(54) ANALYZING ECAP SIGNALS

(71) Applicant: Medtronic, Inc., Minneapolis, MN (US)

(72) Inventors: David A. Dinsmoor, North Oaks, MN (US); Hank Bink, Golden Valley, MN (US); Kristin N. Hageman, Dayton, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/409,455

(22) Filed: Aug. 23, 2021

(65) Prior Publication Data

US 2022/0062639 A1 Mar. 3, 2022

Related U.S. Application Data

(60) Provisional application No. 63/073,678, filed on Sep. 2, 2020.

(51) Int. Cl.
*A61N 1/36* (2006.01)

(52) U.S. Cl.
CPC ..... *A61N 1/36139* (2013.01); *A61N 1/36125* (2013.01)

(58) Field of Classification Search
CPC ............ A61N 1/36139; A61N 1/36125; A61N 1/36031; A61B 5/40; A61B 5/7217; A61B 5/725; A61B 5/05; A61B 5/12; A61B 5/125; A61B 5/38; A61B 5/7257; A61B 5/7264; A61B 5/369
See application file for complete search history.

(56) References Cited

U.S. PATENT DOCUMENTS

| | | | |
|---|---|---|---|
| 5,603,726 | A | 2/1997 | Schulman et al. |
| 5,800,465 | A | 9/1998 | Thompson et al. |
| 6,157,861 | A | 12/2000 | Faltys et al. |
| 6,205,360 | B1 | 3/2001 | Carter |
| 6,289,247 | B1 | 9/2001 | Faltys et al. |

(Continued)

FOREIGN PATENT DOCUMENTS

| | | |
|---|---|---|
| EP | 2396072 B1 | 3/2013 |
| EP | 3013413 A1 | 5/2016 |

(Continued)

OTHER PUBLICATIONS

"St. Jude's Prodigy Neurostimulator with Burst Technology," Medgadget, http://www.medgadget.com, Mar. 20, 2014, 4 pp.

(Continued)

*Primary Examiner* — Carl H Layno
*Assistant Examiner* — Anh-Khoa N Dinh
(74) *Attorney, Agent, or Firm* — Shumaker & Sieffert, P.A.

(57) ABSTRACT

Systems, devices, and techniques are configured for analyzing evoked compound action potentials (ECAP) signals to assess the effect of a delivered electrical stimulation signal. In one example, a system includes processing circuitry configured to receive ECAP information representative of an ECAP signal sensed by sensing circuitry, and determine, based on the ECAP information, that the ECAP signal includes at least one of an N2 peak, P3 peak, or N3 peak. The processing circuitry may then control delivery of electrical stimulation based on at least one of the N2 peak, P3 peak, or N3 peak.

21 Claims, 13 Drawing Sheets

(56) References Cited

U.S. PATENT DOCUMENTS

| | | |
|---|---|---|
| 6,314,325 B1 | 11/2001 | Fitz |
| 6,421,566 B1 | 7/2002 | Holsheimer |
| 6,505,078 B1 | 1/2003 | King et al. |
| 6,675,046 B2 | 1/2004 | Holsheimer |
| 6,850,802 B2 | 2/2005 | Holsheimer |
| 6,988,006 B2 | 1/2006 | King et al. |
| 7,076,292 B2 | 7/2006 | Forsberg |
| 7,206,640 B1 | 4/2007 | Overstreet |
| 7,333,858 B2 | 2/2008 | Killian et al. |
| 7,577,480 B2 | 8/2009 | Zeijlemaker |
| 7,616,999 B2 | 11/2009 | Overstreet et al. |
| 7,657,318 B2 | 2/2010 | King et al. |
| 7,689,289 B2 | 3/2010 | King |
| 7,742,810 B2 | 6/2010 | Moffitt et al. |
| 7,792,583 B2 | 9/2010 | Miesel et al. |
| 8,036,747 B2 | 10/2011 | Thacker et al. |
| 8,090,446 B2 | 1/2012 | Fowler et al. |
| 8,504,150 B2 | 8/2013 | Skelton |
| 8,620,441 B2 | 12/2013 | Greenberg et al. |
| 8,676,329 B2 | 3/2014 | Wacnik et al. |
| 8,694,108 B2 | 4/2014 | Alataris et al. |
| 8,708,934 B2 | 4/2014 | Skelton et al. |
| 8,712,533 B2 | 4/2014 | Alataris et al. |
| 8,712,534 B2 | 4/2014 | Wei |
| 8,751,009 B2 | 6/2014 | Wacnik |
| 8,897,888 B2 | 11/2014 | Parker et al. |
| 8,923,984 B2 | 12/2014 | Parker et al. |
| 9,002,460 B2 | 4/2015 | Parker |
| 9,072,910 B2 | 7/2015 | Parker et al. |
| 9,089,714 B2 | 7/2015 | Robinson |
| 9,089,715 B2 | 7/2015 | Parker et al. |
| 9,138,582 B2 | 9/2015 | Doan et al. |
| 9,155,892 B2 | 10/2015 | Parker et al. |
| 9,283,373 B2 | 3/2016 | Parker et al. |
| 9,302,112 B2 | 4/2016 | Bornzin et al. |
| 9,339,655 B2 | 5/2016 | Carbunaru |
| 9,364,667 B1 | 6/2016 | Dinsmoor et al. |
| 9,381,356 B2 | 7/2016 | Parker et al. |
| 9,386,934 B2 | 7/2016 | Parker et al. |
| 9,387,325 B1 | 7/2016 | Min et al. |
| 9,566,439 B2 | 2/2017 | Single et al. |
| 9,597,507 B2 | 3/2017 | Johanek et al. |
| 9,700,713 B2 | 7/2017 | Robinson et al. |
| 9,872,990 B2 | 1/2018 | Parker et al. |
| 9,993,646 B2 | 6/2018 | Parramon et al. |
| 10,183,168 B2 | 1/2019 | Baru et al. |
| 10,569,088 B2 | 2/2020 | Dinsmoor et al. |
| 10,933,242 B2 | 3/2021 | Torgerson |
| 2004/0267333 A1 | 12/2004 | Kronberg |
| 2008/0221640 A1 | 9/2008 | Overstreet et al. |
| 2008/0300655 A1 | 12/2008 | Cholette |
| 2011/0054570 A1 | 3/2011 | Lane |
| 2011/0071589 A1 | 3/2011 | Starkebaum et al. |
| 2011/0077712 A1 | 3/2011 | Killian |
| 2011/0125223 A1 | 5/2011 | Carbunaru et al. |
| 2012/0155188 A1 | 6/2012 | Buettner et al. |
| 2013/0208390 A1 | 8/2013 | Singh et al. |
| 2013/0268021 A1 | 10/2013 | Moffitt |
| 2013/0289664 A1 | 10/2013 | Johanek |
| 2013/0289683 A1 | 10/2013 | Parker et al. |
| 2014/0005753 A1 | 1/2014 | Carbunaru |
| 2014/0025146 A1 | 1/2014 | Alataris et al. |
| 2014/0031896 A1 | 1/2014 | Alataris et al. |
| 2014/0031905 A1 | 1/2014 | Irazoqui et al. |
| 2014/0074189 A1 | 3/2014 | Moffitt |
| 2014/0142656 A1 | 5/2014 | Alataris et al. |
| 2014/0142673 A1 | 5/2014 | Alataris et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243924 A1 | 8/2014 | Zhu et al. |
| 2014/0243926 A1 | 8/2014 | Carcieri et al. |
| 2014/0243931 A1 | 8/2014 | Parker et al. |
| 2014/0277282 A1 | 9/2014 | Jaax |
| 2014/0288577 A1 | 9/2014 | Robinson et al. |
| 2014/0293737 A1 | 10/2014 | Parker et al. |
| 2014/0296936 A1 | 10/2014 | Alataris et al. |
| 2014/0324143 A1 | 10/2014 | Robinson et al. |
| 2014/0371813 A1 | 12/2014 | King et al. |
| 2014/0378941 A1 | 12/2014 | Su et al. |
| 2014/0379043 A1 | 12/2014 | Howard |
| 2015/0005842 A1 | 1/2015 | Lee et al. |
| 2015/0012068 A1 | 1/2015 | Bradley et al. |
| 2015/0032181 A1 | 1/2015 | Baynham et al. |
| 2015/0057729 A1 | 2/2015 | Parker et al. |
| 2015/0127062 A1 | 5/2015 | Holley et al. |
| 2015/0179177 A1 | 6/2015 | Nagao |
| 2015/0282725 A1 | 10/2015 | Single |
| 2015/0313487 A1 | 11/2015 | Single et al. |
| 2015/0360031 A1 | 12/2015 | Bornzin et al. |
| 2015/0374999 A1 | 12/2015 | Parker et al. |
| 2016/0082252 A1 | 3/2016 | Hershey et al. |
| 2016/0121124 A1 | 5/2016 | Johanek et al. |
| 2016/0129272 A1 | 5/2016 | Hou et al. |
| 2016/0136420 A1 | 5/2016 | Brink et al. |
| 2016/0157769 A1 | 6/2016 | Min et al. |
| 2016/0158550 A1 | 6/2016 | Hou et al. |
| 2016/0166164 A1 | 6/2016 | Obradovic et al. |
| 2016/0175594 A1 | 6/2016 | Min et al. |
| 2016/0206883 A1 | 7/2016 | Bornzin et al. |
| 2016/0287126 A1 | 10/2016 | Parker et al. |
| 2016/0287182 A1 | 10/2016 | Single |
| 2016/0346534 A1 | 12/2016 | Isaacson et al. |
| 2016/0361542 A1 | 12/2016 | Kaula et al. |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0173332 A1 | 6/2017 | Overstreet |
| 2017/0209695 A1 | 7/2017 | Solomon |
| 2017/0216587 A1 | 8/2017 | Parker |
| 2017/0216602 A1 | 8/2017 | Waataja et al. |
| 2017/0296823 A1 | 10/2017 | Hershey et al. |
| 2017/0361101 A1 | 12/2017 | Single |
| 2017/0361103 A1 | 12/2017 | Hadjiyski |
| 2018/0056073 A1 | 3/2018 | Torgerson |
| 2018/0078769 A1 | 3/2018 | Dinsmoor et al. |
| 2018/0110987 A1 | 4/2018 | Parker |
| 2018/0117335 A1 | 5/2018 | Parker et al. |
| 2018/0126169 A1 | 5/2018 | Hou et al. |
| 2018/0132760 A1 | 5/2018 | Parker |
| 2019/0099601 A1 | 4/2019 | Torgerson |
| 2019/0099602 A1* | 4/2019 | Esteller ............... A61N 1/36175 |
| 2019/0105496 A1 | 4/2019 | Min et al. |
| 2019/0209844 A1* | 7/2019 | Esteller ............... A61N 1/36132 |
| 2019/0388692 A1 | 12/2019 | Dinsmoor et al. |
| 2019/0388695 A1 | 12/2019 | Dinsmoor et al. |
| 2020/0171312 A1 | 6/2020 | Dinsmoor et al. |
| 2020/0171313 A1 | 6/2020 | Dinsmoor et al. |
| 2021/0101007 A1 | 4/2021 | Hamner et al. |
| 2021/0121698 A1 | 4/2021 | Dinsmoor et al. |
| 2021/0121700 A1 | 4/2021 | Dinsmoor et al. |

FOREIGN PATENT DOCUMENTS

| | | |
|---|---|---|
| EP | 3024540 B1 | 10/2018 |
| WO | 2002009808 A1 | 2/2002 |
| WO | 2010058178 A1 | 5/2010 |
| WO | 2012155188 A1 | 11/2012 |
| WO | 2014210373 A1 | 12/2014 |
| WO | 2015143509 A1 | 10/2015 |
| WO | 2015179177 A1 | 11/2015 |
| WO | 2015179281 A2 | 11/2015 |
| WO | 2016090420 A1 | 6/2016 |
| WO | 2016090436 A1 | 6/2016 |
| WO | 2016191808 A1 | 12/2016 |
| WO | 2017100866 A1 | 6/2017 |
| WO | 2017106503 A1 | 6/2017 |
| WO | 2017173493 A1 | 10/2017 |
| WO | 2017184238 A1 | 10/2017 |
| WO | 2017219096 A1 | 12/2017 |
| WO | 2018/080754 A1 | 5/2018 |
| WO | 2018080753 A1 | 5/2018 |
| WO | 2018106813 A1 | 6/2018 |

(56) References Cited

FOREIGN PATENT DOCUMENTS

| WO | 2019231794 A1 | 12/2019 |
|---|---|---|
| WO | 2019231796 A1 | 12/2019 |
| WO | 2021081414 A1 | 4/2021 |

OTHER PUBLICATIONS

Abejon et al., "Back pain coverage with spinal cord stimulation: A different treatment for each patient," International Neuromodulation Society, Jun. 10, 2015; 567, Abstract Only, 1 pp.
Abeloos MD "High density stimulation as an alternative to uncomfortable cervical tonic spinal cord stimulation: case report," International Neuromodulation Society 12th World Congress, Jun. 11-15, 2015, Abstract Only, 1 pp.
Agnesi et al., "Local Glutamate Release in the Rat Ventral Lateral Thalamus Evoked by High-Frequency Stimulation," Journal of Neural Engineering, vol. 7, No. 2, Apr. 2010, 20 pp.
Breel et al., "High Density Stimulation: A novel programming paradigm for the treatment of chronic pain," International Neuromodulation Society (INS) 12th World Congress; Jun. 9, 2015, Abstract Only, 1 pp.
Crosby et al., "Modulation of activity and conduction in single dorsal column axons by kilohertz-frequency spinal cord stimulation," American Physiological Society, published online Oct. 19, 2016, 27 pp.
Cuellar et al., "Effect of High-Frequency Alternating Current on Spinal Afferent Nociceptive Transmission," Neuromodulation: Technology at the Neural Interface, vol. 16, No. 4, DOI: 10.1111/ner.12015, Nov. 6, 2012, pp. 318-327.
Cui et al., "Effect of spinal cord stimulation on tactile hypersensitivity in mononeuropathic rats is potentiated by simultaneous GABA. sub B. and adenosine receptor activation," ELSEVIER, Neuroscience Letters, vol. 247, Apr. 1998, pp. 183-186.
Cui et al., "Spinal cord stimulation attenuates augmented dorsal horn release of excitatory amino acids in mononeuropathy via a GABAergic mechanism," International Association for the STudy of Pain, Pain, vol. 73, Oct. 1997, pp. 87-95.
De Ridder et al., "Burst spinal cord stimulation for limb and back pain," Science Direct, World Neurosurgery, vol. 80, No. 5, http://dx.doi.org/10.1016/j.wneu.2013.01.040, Nov. 2013, pp. 642-649, e641.
De Ridder et al., "Burst Spinal Cord Stimulation: Toward Paresthesia-Free Pain Suppression," Neurosurgery, vol. 66, No. 5, May 2010, pp. 986-990.
Downey, "Asynchronous Neuromuscular Electrical Stimulation," University of Florida, 2015, accessed on Jul. 18, 2016, 107 pp.
Duyvendak et al., "High density stimulation: a novel programming paradigm for the treatment of chronic back and leg pain," Abstracts, International Neuromodulation Society 12th World Congress, Neuromodulation, vol. 18, Jun. 11-15, 2015, 1 pp.
Gao et al., "Effects of spinal cord stimulation with "standard clinical" and higher frequencies on peripheral blood flow in rats," ELSEVIER, Brain Research, vol. 1313, doi:10.1016/j.brainres.2009.11.072, available online Dec. 3, 2009, pp. 53-61.
Grider et al., "High Frequency (1000 Hz) Stimulation Using Commercially Available Implantable Pulse Generator," North American Neuromodulation Society, No. 198, Dec. 2013, Abstract Only, 2 pp.
Guan et al., "Spinal Cord Stimulation-induced Analgesia: Electrical Stimulation of Dorsal col. and Dorsal Roots Attenuates Dorsal Horn Neuronal Excitability in Neuropathic Rats," The American Society of Anesthesiologists, Inc., Anesthesiology, vol. 113, No. 6, Dec. 2010, pp. 1392-1405.
Guan, "Spinal Cord Stimulation: Neurophysiological and Neurochemical Mechanisms of Action" Current Pain and Headache Reports, Vo. 16, DOI 10.1007s11916-014-0260-4, Mar. 8, 2012, pp. 217-225.
Holsheimer, "Computer modelling of spinal cord stimulation and its contribution to therapeutic efficacy," International Medical Society of Paraplegia, Spinal Cord, vol. 36, Aug. 1998, pp. 531-540.
Hubscher et al., "Convergence and cross talk in urogenital neural circuitries," The American Physiological Society, Journal of Neurophysiology, vol. 110, doi:10.1152/jn.00297.2013, Aug. 7, 2013, pp. 1997-2005.
Hunt et al. "The Molecular Dynamics of Pain Control," MacMillan Magazines, Ltd., Nature Reviews, Neuroscience, vol. 2, No. 2, Feb. 2001, pp. 83-91.
Kemler et al., "Spinal Cord Stimulation in Patients with Chronic Reflex Sympathetic Dystrophy," The New England Journal of Medicine, vol. 343, No. 9, Aug. 31, 2000, pp. 618-624.
Kilgore et al., "Reversible Nerve Conduction Block Using Kilohertz Frequency Alternating Current," International Modulation Society, Neuromodulation, vol. 17, DOI: 10.1111/ner.12100, Aug. 2013, pp. 242-255.
Kumar et al., "Spinal cord stimulation versus conventional medical management for neuropathic pain: a multicentre randomised controlled trial in patients with failed back surgery syndrome," International Association for the Study of Pain, Pain, vol. 132, No. 102, Jul. 2007, pp. 179-188.
Likar et al., "High density spinal cord stimulation: a multi-center experience," Abstracts, International Neuromodulation Society 12th World Congress, Neuromodulation, vol. 18, Jun. 11-15, 2015, 1 pp.
Maeda et al., "Increased c-fos immunoreactivity in the spinal cord and brain following spinal cord stimulation is frequency-dependent," ELSEVIER, Brain Research, vol. 1259, Mar. 9, 2009, pp. 40-50.
Maeda et al., "Low frequencies, but not high frequencies of bi-polar spinal cord stimulation reduce cutaneous and muscle hyperalgesia induced by nerve injury," International Association for the Study of Pain, Pain. Vol. 138, No. 1, Feb. 2008, pp. 143-152.
Maggi et al., "Effect of urethane anesthesia on the micturition reflex in capsaicin-treated rats," ELSEVIER, Journal of the Autonomic Nervous System, vol. 30, No. 3, Jan. 1990, pp. 247-251.
North et al., "Clinical outcomes of 1 kHz subperception spinal cord stimulation (SCS): Results of a prospective randomized controlled crossover trial," Abstracts, International Neuromodulation Society, Neuromodulation, vol. 18, Jun. 2015, 1 pp.
North et al., "Spinal Cord Stimulation versus Repeated Lumbosacral Spine Surgery for Chronic Pain: A Randomized, Controlled Trail," Neurosurgery, vol. 56, No. 1, Jan. 2005, pp. 98-106; discussion 106-107.
Ranck JR. et al., "Which Elements are Excited in Electrical Stimulation of Mammalian Central Nervous System: A Review," ELSEVIER Scientific Publishing Company, Brain Research, vol. 98, No. 3, Nov. 21, 1975, pp. 417-440.
Replogle MD. et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication s not in issue.
Sato et al., "Spinal cord stimulation reduces hypersensitivity through activation of opioid receptors in a frequency-dependent manner," European Journal of Pain, vol. 4, Apr. 2013, pp. 551-561.
Schu et al., "A Prospective, Randomised, Double-blind, Placebo-controlled Study to Examine the Effectiveness of Burst Spinal Cord Stimulation Patterns for the Treatment of Failed Back Surgery Syndrome," International Neuromodulation Society, Neuromodulation, vol. 17, No. 5, Apr. 2014, pp. 443-450.
Shechter et al., "Conventional and Kilohertz-frequency Spinal Cord Stimulation Produces Intensity- and Frequency-dependent Inhibition of Mechanical Hypersensitivity in a Rat Model of Neuropathic Pain," Anesthesiology, vol. 119, No. 2, Aug. 2013, pp. 422-432.
Sluka, et al., "High-frequency, but not low-frequency, transcutaneous electrical nerve stimulation reduces aspartate and glutamate release in the spinal cord dorsal horn," Journal of Neurochemistry, vol. 95, No. 6, Oct. 17, 2005, pp. 1794-1801.
Smith et al., "Successful Use of High-Frequency Spinal Cord Stimulation Following Traditional Treatment Failure," Stereotactic and Functional Neurosurgery, vol. 93, No. 3, Apr. 1, 2015, pp. 190-193.

(56) References Cited

OTHER PUBLICATIONS

Snellings et al., "Effects of stimulation site and stimulation parameters on bladder inhibition by electrical nerve stimulation," BJU International, Jul. 2012, pp. 136-143.

Song et al., "Efficacy of Kilohertz-Frequency and Conventional Spinal Cord Stimulation in Ray Models of Different Pain Conditions," International Neuromodulation Society, Neuromodulation, vol. 17, No. 3, Jan. 2014, pp. 226-234.

Sweet et al., "High Frequency vs. Burst Stimulation Patterns for Dorsal Column Stimulation: The Importance of Charge," American Association of Neurological Surgeons, Abstract, Apr. 4, 2014, 2 pp.

Vallejo et al., "Effects of Phase Polarity and Charge Balance Spinal Cord Stimulation on Behavior and Gene Expression in a Rat Model of Neuropathic Pain," Neuromodulation: Technology at the Neural Interface, vol. 23, No. 1, Apr. 2019, 10 pp.

Walter et al., "Inhibiting the Hyperrflexic Bladder With Electrical Stimulation in a Spinal Animal Mode," Neurourology and Urodynamics, vol. 12, doi:10.1002/nau.1930120306, Oct. 19, 1992, pp. 241-253.

Wille et al., "Altering Conventional to High Density Spinal Cord Stimulation: An Energy Dose-Response Relationship in Neuropathic Pain Therapy," International Neuromodulation Society, Neuromodulation 2016, Aug. 2016, 9 pp.

Woock et al., "Activation and inhibition of the micturition reflex by penile afferents in the cat," The American Journal of Physiology—Regulatory, Integrative and Comparative Physiology, vol. 294, Apr. 23, 2008, pp. R1880-R1889.

Youn et al., The Effect of High-Frequency Stimulation on Sensory Thresholds in Chronic Pain Patients, Stereotact Funct Neurosurg, Oct. 8, 2015, pp. 355-359.

Mens., "Advances in Cochlear Implant Telemetry: Evoked Neural Responses, Electrical Field Imaging, and Technical Integrity," Sage Publications, vol. 11, No. 3, Sep. 2007, 17 pp.

Zeng et al., "Cochlear Implants: System Design, Integration and Evaluation," IEEE Rev Biomed Eng., Jan. 1, 2008, 66 pp.

Akhoun et al., "Electrically Evoked Compound Action Potential Artifact Rejection by Independent Component Analysis: Technique Validation," Hearing Research, Elsevier Science Publishers, vol. 302, XP028573541, ISSN: 0378-5955, DOI: 10.1016/J.HEARES.2013.04.005, Apr. 28, 2013, pp. 60-73.

El Tahry et al., "A Novel Implantable Vagus Nerve Stimulation System (ADNS-300) for Combined Stimulation and Recording of the Vagus Nerve: Pilot Trial at Ghent University Hospital", Epilepsy Research, Elsevier Science Publishers, vol. 92, n.2-3, XP027510539, ISSN: 0920-1211, DOI: 2010.10.007, Dec. 1, 2010, pp. 231-239.

International Search Report and Written Opinion of International Application No. PCT/US2021/047345, dated Dec. 20, 2021, 16 pp.

\* cited by examiner

ANALYZING ECAP SIGNALS

This application claims the benefit of U.S. Provisional Patent Application No. 63/073,678, filed Sep. 2, 2020, the entire contents of which is incorporated herein by reference.

TECHNICAL FIELD

This disclosure generally relates to sensing physiological parameters, and more specifically, analysis of a sensed signal indicative of a physiological parameter.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

Electrical stimulation may be delivered to a patient by the medical device in a train of electrical pulses, and parameters of the electrical pulses may include a frequency, an amplitude, a pulse width, and a pulse shape. An evoked compound action potential (ECAP) is synchronous firing of a population of neurons which occurs in response to the application of a stimulus including, in some cases, an electrical stimulus by a medical device. The ECAP may be detectable as being a separate event from the stimulus itself, and the ECAP may reveal characteristics of the effect of the stimulus on the nerve fibers.

SUMMARY

In general, systems, devices, and techniques are described for analyzing evoked compound action potentials (ECAP) signals to assess the effect of a delivered electrical stimulation signal. A system may then use one or more characteristics of the ECAP signal as feedback to adjust and control subsequent electrical stimulation delivered to a patient. When a patient moves, the distance between implanted electrodes and target nerves changes. For example, electrodes implanted along the spinal column are closer to the spinal cord when a subject lies in a supine posture state as compared to a standing posture state. Similarly, the implanted electrodes may move closer to the spinal cord when a subject coughs or sneezes. Therefore, one or more characteristics of the ECAP signal changes according to the stimulation pulse that evoked the ECAP signal and the distance between the electrodes and the nerves.

Devices and systems described herein first analyze an ECAP signal to determine which features should be identified and used to determine one or more characteristics of the ECAP signal that can be effective for feedback in a closed-loop control system. The ECAP signal may include one or more detectable positive peaks and one or more detectable negative peaks identified in increasing latency from the stimulus as the P1, N1, P2, N2, P3, N3, etc. peaks. In some examples, the pulse width of the stimulation pulse that elicits the ECAP signal is too long and is detected as an artifact that partially or completely covers one or more of the peaks. In this situation, a system (e.g., an implantable medical device (IMD) may utilize later occurring peaks (e.g., N2, P3, N3, etc.) in the ECAP signal to determine the characteristic value of the ECAP signal. The system may select the peaks of the ECAP signal that are greater than a threshold distance (or time) from the artifact to avoid corruption in ECAP feature assessment that can occur due to the proximity of the artifact. In some examples, the system can increase the pulse width of the stimulation pulse eliciting ECAP signals until later occurring peaks are detected. The system may then determine a characteristic value of the ECAP signal based on one or more of the selected peaks (e.g., the amplitude between the P2/N2, N2/P3, or P3/N3 pairs) and adjust one or more parameter values that define subsequent electrical stimulation based on the characteristic value.

In one example, a system includes processing circuitry configured to receive evoked compound action potential (ECAP) information representative of an ECAP signal sensed by sensing circuitry; determine, based on the ECAP information, that the ECAP signal includes at least one of an N2 peak, P3 peak, or N3 peak; and control delivery of electrical stimulation based on at least one of the N2 peak, P3 peak, or N3 peak.

In another example, a method includes receiving, by processing circuitry, evoked compound action potential (ECAP) information representative of an ECAP signal sensed by sensing circuitry; determining, by the processing circuitry and based on the ECAP information, that the ECAP signal includes at least one of an N2 peak, P3 peak, or N3 peak; and controlling, by the processing circuitry, delivery of electrical stimulation based on at least one of the N2 peak, P3 peak, or N3 peak.

In another example, a computer-readable medium includes instructions that, when executed, causes processing circuitry to receive evoked compound action potential (ECAP) information representative of an ECAP signal sensed by sensing circuitry; determine, based on the ECAP information, that the ECAP signal includes at least one of an N2 peak, P3 peak, or N3 peak; and control delivery of electrical stimulation based on at least one of the N2 peak, P3 peak, or N3 peak.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

Figure 1:
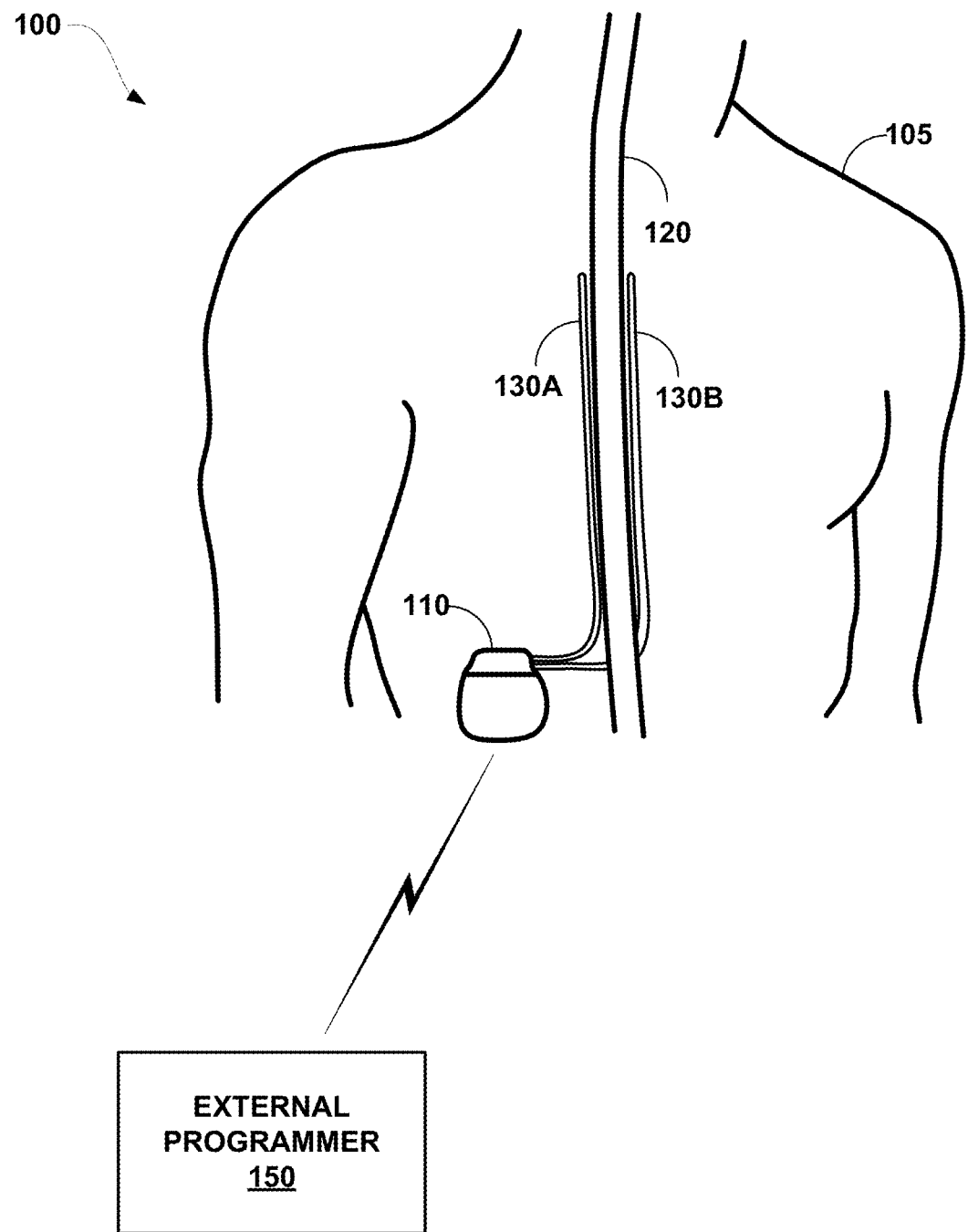
FIG. 1 is a conceptual diagram illustrating an example system that includes an implantable medical device (IMD) configured to deliver spinal cord stimulation (SCS) therapy and an external programmer, in accordance with one or more techniques of this disclosure.

The disclosure describes examples of medical devices, systems, and techniques for analyzing evoked compound action potentials (ECAP) signals to assess the effect of a delivered electrical stimulation signal. Electrical stimulation therapy is typically delivered to a target tissue (e.g., nerves of the spinal cord or muscle) of a patient via two or more electrodes. Parameters of the electrical stimulation therapy (e.g., electrode combination, voltage or current amplitude, pulse width, pulse frequency, etc.) are selected by a clinician and/or the patient to provide relief from various symptoms, such as pain, nervous system disorders, muscle disorders, etc. However, as the patient moves, the distance between the electrodes and the target tissues changes. Since neural recruitment at the nerves is a function of stimulation intensity (e.g., amplitude and/or pulse frequency) and distance between the target tissue and the electrodes, movement of the electrode closer to the target tissue may result in increased neural recruitment (e.g., possible painful sensations or adverse motor function), and movement of the electrode further from the target tissue may result in decreased efficacy of the therapy for the patient. Certain patient postures (which may or may not include patient activity) may be representative of respective distances (or changes in distance) between electrodes and nerves and thus be an informative feedback variable for modulating stimulation therapy.

ECAPs are a measure of neural recruitment because each ECAP signal represents the superposition of electrical potentials generated from a population of axons firing in response to an electrical stimulus (e.g., a stimulation pulse). Changes in a characteristic (e.g., an amplitude of a portion of the signal or area under the curve of the signal) of an ECAP signals occur as a function of how many axons have been activated by the delivered stimulation pulse. For a given set of parameter values that define the stimulation pulse and a given distance between the electrodes and target nerve, the detected ECAP signal may have a certain characteristic value (e.g., amplitude). Therefore, a system can determine that the distance between electrodes and nerves has increased or decreased in response to determining that the measured ECAP characteristic value has increased or decreased. For example, if the set of parameter values stays the same and the ECAP characteristic value of amplitude increases, the system can determine that the distance between electrodes and the nerve has decreased.

In some examples, effective stimulation therapy may rely on a certain level of neural recruitment at a target nerve. This effective stimulation therapy may provide relief from one or more conditions (e.g., patient perceived pain) without an unacceptable level of side effects (e.g., overwhelming perception of stimulation). If the patient changes posture or otherwise engages in physical activity, the distance between the electrodes and the nerve changes as well. This change in distance can cause loss of effective therapy and/or side effects if the parameter values that define stimulation pulses are not adjusted to compensate for the change in distance. A system may change stimulation parameters to compensate for changes to the distance between electrodes and the target nerve, such as increasing stimulation intensity in response the distance increases and decreasing stimulation intensity in response to the distance decreasing.

Although the system may adjust one or more stimulation parameters according to the one or more characteristics of the sensed ECAP signal to compensate for the change in distance between electrodes and nerves, the precision of such adjustments is dependent on accurately determining the characteristics of the ECAP signal. However, the ability to resolve features of the ECAP signal may be affected by contamination by the stimulation artifact (e.g., the detected stimulation pulse overlapping with at least a portion of one or more peaks of the ECAP signal). This contamination becomes more significant with wider pulses, as the stimulation artifact progressively effaces the N1 and P2 features of the ECAP signal. The end result is reduced amplitudes of the N1, and in some examples the P2 peak, which results in lower amplitude differences between the N1 and P2 peaks (e.g., lower signal to noise ratio). In some examples, shorter pulses may limit the effect of the artifact on the N1 or P2 peaks, but shorter pulse widths require larger amplitudes to elicit an ECAP signal and may be more perceptible by the patient.

As described herein, systems, devices, and techniques are described for analyzing an ECAP signal sensed from the patient in order to determine one or more characteristic values of the ECAP signal. A medical device, such as an implantable medical device, may analyze the ECAP signal to determine which one or more features of the ECAP signal should be used to determine a characteristic value for the ECAP signal. In cases where the N1 and/or P2 peak is encumbered (or affected) by artifact or a longer pulse width is desired for the stimulation pulse, the medical device may utilize later occurring features in the ECAP signal, such as the N2, P3, and/or N3 peak. These later occurring features may be resolved as these later features manifest further (or later in time) from the artifact. These later occurring features of the ECAP signal are generally smaller in amplitude than the N1 and P2 peaks and may not be present in detected ECAP signals from all subjects. A neurophysiologic effect which aids sensing of the ECAP with wider pulse widths is that the onset of neural activation is a function of the charge sourced onto the neural target. The latency of an ECAP signal resulting from a higher amplitude, narrow stimulus will be shorter than that of a lower amplitude, wider stimulus constant charge. This effect allows longer stimulation pulse widths to be used, with acceptable encroachment by the stimulation artifact, than would be possible if the ECAP signal always occurred at the same latency with respect to the leading edge of the stimulation pulse.

In this manner, the medical device may determine which features (e.g., peaks, peak-to-peak amplitudes, area under each peak, etc.) of the ECAP signal should be used to determine a characteristic value of the ECAP signal. The amplitude between the N1 and P2 peaks may be used as the characteristic value of an ECAP signal. However, the medical device can determine when the stimulation artifact encumbers one or both of the N1 and P2 peaks. Such an encumbrance may reduce the amplitudes of, and/or corrupt, one or both of the N1 and P2 peaks and prevent an accurate determination of the ECAP signal. The medical device may determine that the stimulation artifact encumbers the N1 or P2 peaks in response to determining that the distance, or time, from the stimulation artifact to the N1 and/or P2 peak is less than a predetermined distance or time. If the medical device determines that one or more of the later occurring peaks (e.g., N2, P3, N3, etc.) in the ECAP signal is detectable, the medical device may use one or more of these later occurring peaks to determine the characteristic value of the ECAP signal. In this manner, the system may select the peaks of the ECAP signal that are greater than a threshold distance (or time) from the artifact to avoid reduction in peak amplitude that can occur due to the proximity of the artifact.

In some examples, the medical device can increase the pulse width of the stimulation pulse eliciting ECAP signals until later occurring peaks are detected. The medical device may perform this increase the pulse width in response to determination that the stimulation artifact encumbers an earlier occurring peak (e.g., the N1 or P2 peak). In other examples, the medical device may increase the pulse width to identify alternative stimulation parameters that may be less perceptible, or more acceptable to, the subject for eliciting detectable ECAP signals. For example, wider pulse widths may require lower amplitudes to elicit a detectable ECAP signal. Once the pulse width is long enough for later occurring peaks to be detected, the system may then determine a characteristic value of the ECAP signal based on one or more of the selected peaks (e.g., the amplitude between the P2/N2, N2/P3, or P3/N3 pairs) and adjust one or more parameter values that define subsequent electrical stimulation based on the characteristic value.

The IMD may utilize the characteristic value of the ECAP signal as feedback that informs one or more aspects of electrical stimulation, such as intensity of subsequent electrical stimulation therapy. For example, the IMD may adjust one or more parameter values that define subsequent electrical stimulation based on the characteristic value. The IMD may monitor the characteristic values from respective ECAP signals over time and increase or decrease parameter values in order to maintain a target characteristic value or range of values. In another example, the IMD may monitor the characteristic values from ECAP signals over time and reduce a stimulation parameter value when the characteristic value exceeds a threshold in order to reduce the likelihood of overstimulation as perceived by the patient. The IMD may employ these or other control policies based on the determined characteristic value from sensed ECAP signals.

In some examples, the ECAPs detected by an IMD may be ECAPs elicited by stimulation pulses intended to contribute to therapy of a patient or separate pulses configured to elicit ECAPs that are detectable by the IMD. Nerve impulses detectable as the ECAP signal travel quickly along the nerve fiber after the delivered stimulation pulse first depolarizes the nerve. If the stimulation pulse delivered by first electrodes has a pulse width that is too long, different electrodes configured to sense the ECAP will sense the stimulation pulse itself as an artifact (e.g., detection of delivered charge itself as opposed to detection of a physiological response to the delivered stimulus) that obscures most or all of the lower amplitude ECAP signal. However, the ECAP signal loses fidelity as the electrical potentials propagate from the electrical stimulus because different nerve fibers propagate electrical potentials at different speeds. Therefore, sensing the ECAP at a far distance from the stimulating electrodes may avoid the artifact caused by a stimulation pulse with a long pulse width, but the ECAP signal may lose fidelity needed to detect changes to the ECAP signal that occur when the electrode to target tissue distance changes. In other words, the system may not be able to identify, at any distance from the stimulation electrodes, ECAPs from stimulation pulses configured to provide a therapy to the patient.

In some examples, ECAPs are detectable from pulses intended to contribute to the therapy of a patient. However, when these therapy pulses cause artifacts that interfere with the IMD's ability to detect the ECAP, the IMD may be configured to deliver pulses separate from pulses intended to contribute to therapy for the purpose of detecting ECAPs without interference from the pulses themselves. The pulses configured to elicit detectable ECAPs may be referred to as control pulses, and the pulses from which ECAPs are not detectable, but otherwise are adjusted according to characteristics of the ECAP signals, may be referred to as informed pulses. In this manner, the plurality of control pulses may or may not contribute to therapy received by the patient, and the informed pulses may generally be configured to contribute to therapy received by the patient. Therefore, the IMD or other component associated with the medical device may determine values of one or more stimulation parameters that at least partially define the informed pulses based on an ECAP signal elicited by a control pulse instead. For example, the control pulses may be configured to elicit ECAPs used to detect the posture state of the patient. In this manner, the informed pulse may be informed by the ECAP elicited from a control pulse. The medical device or other component associated with the medical device may determine values of one or more stimulation parameters that at least partially define the control pulses based on an ECAP signal elicited by previous control pulse.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal than may have a sinusoidal waveform or other continuous waveform.

FIG. 1 is a conceptual diagram illustrating an example system 100 that includes an implantable medical device (IMD) 110 configured to deliver spinal cord stimulation (SCS) therapy and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. In some examples, the stimulation signals, or pulses, may be configured to elicit detectable ECAP signals that IMD 110 may use to determine the posture state occupied by patient 105 and/or determine how to adjust one or more parameters that define stimulation therapy. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter set of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, voltage or current amplitude, pulse frequency, pulse width, pulse shape of stimulation delivered by the electrodes. These stimulation parameters values that make up the stimulation parameter set that defines pulses may be predetermined parameter values defined by a user and/or automatically determined by system 100 based on one or more factors or user input.

If control pulses separate from the informed pulses (together different types of stimulation pulses) used for therapy are needed to elicit a detectable ECAP signal, system 100 may employ an ECAP test stimulation program that defines stimulation parameter values that define control pulses delivered by IMD 110 through at least some of the electrodes of leads 130. These stimulation parameter values may include information identifying which electrodes have been selected for delivery of control pulses, the polarities of the selected electrodes, i.e., the electrode combination for the program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each ECAP test stimulation program are configured to evoke a compound action potential from nerves. In some examples, the ECAP test stimulation program defines when the control pulses are to be delivered to the patient based on the frequency and/or pulse width of the informed pulses. However, the stimulation defined by each ECAP test stimulation program are not intended to provide or contribute to therapy for the patient. In addition, the ECAP test stimulation program may define the control pulses used for each sweep of pulses that are used to determine the posture state of the patient.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, lead 130 includes one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 110 is configured to generate and deliver electrical stimulation therapy to a target stimulation site within patient 105 via the electrodes of leads 130 to patient 105 according to one or more therapy stimulation programs. A therapy stimulation program defines values for one or more parameters (e.g., a parameter set) that define an aspect of the therapy delivered by IMD 110 according to that program. For example, a therapy stimulation program that controls delivery of stimulation by IMD 110 in the form of pulses may define values for voltage or current pulse amplitude, pulse width, pulse rate (e.g., pulse frequency), electrode combination, pulse shape, etc. for stimulation pulses delivered by IMD 110 according to that program.

Furthermore, IMD 110 may be configured to deliver control stimulation to patient 105 via a combination of electrodes of leads 130, alone or in combination with an electrode carried by or defined by an outer housing of IMD 110 in order to detect ECAP signals (e.g., control pulses and/or informed pulses). The tissue targeted by the stimulation may be the same or similar tissue targeted by the electrical stimulation therapy, but IMD 110 may deliver stimulation pulses for ECAP signal detection via the same, at least some of the same, or different electrodes. Since control stimulation pulses can be delivered in an interleaved manner with informed pulses (e.g., when the pulses configured to contribute to therapy interfere with the detection of ECAP signals or pulse sweeps intended for posture state detection via ECAP signals do not correspond to pulses intended for therapy purposes), a clinician and/or user may select any desired electrode combination for informed pulses. Like the electrical stimulation therapy, the control stimulation may be in the form of electrical stimulation pulses or continuous waveforms. In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes on leads 130. In cases where the control stimulation pulses are applied to spinal cord 120, the signal may be sensed by IMD 110 from spinal cord 120.

IMD 110 can deliver control stimulation to a target stimulation site within patient 105 via the electrodes of leads 130 according to one or more ECAP test stimulation programs. The one or more ECAP test stimulation programs may be stored in a storage device of IMD 110. Each ECAP test program of the one or more ECAP test stimulation programs includes values for one or more parameters that define an aspect of the control stimulation delivered by IMD 110 according to that program, such as current or voltage amplitude, pulse width, pulse frequency, electrode combination, and, in some examples timing based on informed pulses to be delivered to patient 105. In some examples, the ECAP test stimulation program may also define the number of pules and parameter values for each pulse of multiple pulses within a pulse sweep configured to obtain a plurality of ECAP signals for respective pulses in order to obtain the growth curve that IMD 110 may use to determine the current posture state of the patient. In some examples, IMD 110 delivers control stimulation to patient 105 according to multiple ECAP test stimulation programs.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control stimulation, such as electrical stimulation therapy (e.g., informed pulses) and/or control stimulation (e.g., control pulses). For example, external programmer 150 may transmit therapy stimulation programs, ECAP test stimulation programs, stimulation parameter adjustments, therapy stimulation program selections, ECAP test program selections, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

In some examples, IMD 110 may detect ECAP signals from pulses delivered for the purpose of providing therapy to the patient. In other examples, the pulses configured to provide therapy to the patient may interfere with the detection of the ECAP signals. In this manner, the therapy pulses may be referred to as informed pulses because the parameter values that define the informed pulses may be determined by IMD 110 according to ECAP signals elicited from different control pulses.

In one example, each informed pulse may have a pulse width greater than approximately 300 µs, such as between approximately 300 µs and 1000 µs (i.e., 1 millisecond) in some examples. At these pulse widths, IMD 110 may not sufficiently detect an ECAP signal because the informed pulse is also detected as an artifact that obscures the ECAP signal. When pulses intended to provide therapy have these longer pulse widths, IMD 110 may deliver control stimulation in the form of control pulses in order to detect ECAP signals. The control pulses may have pulse widths of less than the interfering therapy pulses (e.g., less than approximately 300 µs), such as a bi-phasic pulse with each phase having a duration of approximately 100 µs. In some examples, the pulse width (including both phases) may be from approximately 30 µs to approximately 300 µs. Since the control pulses may have shorter pulse widths than the informed pulses, the ECAP signal may be sensed and identified following each control pulse and used to inform IMD 110 about any changes that should be made to the informed pulses (and control pulses in some examples). In general, the term "pulse width" refers to the collective duration of every phase, and interphase interval when appropriate, of a single pulse. A single pulse includes a single phase in some examples (i.e., a monophasic pulse) or two or more phases in other examples (e.g., a bi-phasic pulse or a tri-phasic pulse). The pulse width defines a period of time beginning with a start time of a first phase of the pulse and concluding with an end time of a last phase of the pulse (e.g., a biphasic pulse having a positive phase lasting 100 µs, a negative phase lasting 100 µs, and an interphase interval lasting 30 µs defines a pulse width of 230 µs). In other examples, a biphasic pulse may have a positive phase lasting 120 µs, a negative phase lasting 120 µs, and an interphase interval lasting 30 µs defines a pulse width of 270 µs.

In this disclosure, efficacy of electrical stimulation therapy may be indicated by one or more characteristics of an action potential that is evoked by a stimulation pulse delivered by IMD 110 (i.e., a characteristic value of the ECAP signal). Electrical stimulation therapy delivery by leads 130 of IMD 110 may cause neurons within the target tissue to evoke a compound action potential that travels up and down the target tissue, eventually arriving at sensing electrodes of IMD 110. Furthermore, stimulation pulses (e.g., informed pulses and/or control pulses) may also elicit at least one ECAP signal, and ECAPs responsive to control stimulation may also be a surrogate for the effectiveness of the therapy and/or the intensity perceived by the patient. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control stimulation pulses.

Example techniques for adjusting stimulation parameter values for informed pulses (e.g., pulses configured to contribute to therapy for the patient) are based on comparing the value of a characteristic of a measured ECAP signal to a target ECAP characteristic value for a previous control pulse. During delivery of control stimulation pulses defined by one or more ECAP test stimulation programs, IMD 110, via two or more electrodes interposed on leads 130, senses electrical potentials of tissue of the spinal cord 120 of patient 105 to measure the electrical activity of the tissue. IMD 110 senses ECAPs from the target tissue of patient 105, e.g., with electrodes on one or more leads 130 and associated sense circuitry. In some examples, IMD 110 receives a signal indicative of the ECAP from one or more sensors, e.g., one or more electrodes and circuitry, internal or external to patient 105. Such an example signal may include a signal indicating an ECAP of the tissue of patient 105. Examples of the one or more sensors include one or more sensors configured to measure a compound action potential of patient 105, or a physiological effect indicative of a compound action potential. For example, to measure a physiological effect of a compound action potential, the one or more sensors may be an accelerometer, a pressure sensor, a bending sensor, a sensor configured to detect a posture of patient 105, or a sensor configured to detect a respiratory function of patient 105. However, in other examples, external programmer 150 receives a signal indicating a compound action potential in the target tissue of patient 105 and transmits a notification to IMD 110.

In the example of FIG. 1, IMD 110 described as performing a plurality of processing and computing functions. However, external programmer 150 instead may perform one, several, or all of these functions. In this alternative example, IMD 110 functions to relay sensed signals to external programmer 150 for analysis, and external programmer 150 transmits instructions to IMD 110 to adjust the one or more parameters defining the electrical stimulation therapy based on analysis of the sensed signals. For example, IMD 110 may relay the sensed signal indicative of an ECAP to external programmer 150. External programmer 150 may compare the parameter value of the ECAP to the target ECAP characteristic value, and in response to the comparison, external programmer 150 may instruct IMD 110 to adjust one or more stimulation parameter that defines the electrical stimulation informed pulses and, in some examples, control pulses, delivered to patient 105.

In the example techniques described in this disclosure, the control stimulation parameters and the target ECAP characteristic values may be initially set at the clinic but may be set and/or adjusted at home by patient 105. For example, the target ECAP characteristics may be changed to match or be a fraction of a stimulation threshold. In some examples, target ECAP characteristics may be specific to respective different posture states of the patient. Once the target ECAP characteristic values are set, the example techniques allow for automatic adjustment of parameter values that define stimulation pulses (e.g., control pulses and/or informed pulses) to maintain consistent volume of neural activation and consistent perception of therapy for the patient when the electrode-to-neuron distance changes. The ability to change the stimulation parameter values may also allow the therapy to have long term efficacy, with the ability to keep the intensity of the stimulation (e.g., as indicated by the ECAP) consistent by comparing the measured ECAP values to the target ECAP characteristic value. In addition, or alternatively, to maintaining stimulation intensity, IMD 110 may monitor the characteristic values of the ECAP signals to limit one or more parameter values that define stimulation pulses. IMD 110 may perform these changes without intervention by a physician or patient 105.

In some examples, the system changes the target ECAP characteristic value over a period of time, such as according to a change to a stimulation threshold (e.g., a perception threshold or detection threshold). The system may be programmed to change the target ECAP characteristic in order to adjust the intensity of stimulation pulses to provide varying sensations to the patient (e.g., increase or decrease the volume of neural activation). Although the system may change the target ECAP characteristic value, received ECAP signals may still be used by the system to adjust one or more parameter values of the stimulation pulse (e.g., informed pulses and/or control pulses) in order to meet the target ECAP characteristic value.

One or more devices within system 100, such as IMD 110 and/or external programmer 150, may perform various functions as described herein. For example, IMD 110 may include stimulation circuitry configured to deliver electrical stimulation, sensing circuitry configured to sense a plurality ECAP signals, and processing circuitry. The processing circuitry may be configured to control the stimulation circuitry to deliver a plurality of electrical stimulation pulses having different amplitude values and control the sensing circuitry to detect, after delivery of each electrical stimulation pulse of the plurality of electrical stimulation pulses, a respective ECAP signal of the plurality of ECAP signals. The processing circuitry of IMD 110 may then determine, based on the plurality of ECAP signals, a posture state of the patient.

In some examples, IMD 110 may include the stimulation circuitry, the sensing circuitry, and the processing circuitry. However, in other examples, one or more additional devices may be part of the system that performs the functions described herein. For example, IMD 110 may include the stimulation circuitry and the sensing circuitry, but external programmer 150 or other external device may include the processing circuitry that at least determines the posture state of the patient. IMD 110 may transmit the sensed ECAP signals, or data representing the ECAP signal, to external programmer 150, for example. Therefore, the processes described herein may be performed by multiple devices in a distributed system. In some examples, system 100 may include one or more electrodes that deliver and/or sense electrical signals. Such electrodes may be configured to sense the ECAP signals. In some examples, the same electrodes may be configured to sense signals representative of transient movements of the patient. In other examples, other sensors, such as accelerometers, gyroscopes, or other movement sensors may be configured to sense movement of the patient that indicates the patient may have transitioned to a different posture state, by which the target characteristic value may have changed accordingly.

As described herein, the processing circuitry of IMD 110 may be configured to determine characteristic values for the plurality of ECAP signals detected after each of the plurality of electrical stimulation pulses. The characteristic value for each ECAP signal is a representation of the ECAP signal.

In some examples, system 100, which may include IMD 110 and/or external programmer 150, includes a stimulation generator configured to deliver a stimulation pulse to a patient and sensing circuitry configured to sense the ECAP signal elicited from the stimulation pulse. System 100 may also include processing circuitry configured to receive ECAP information representative of an ECAP signal sensed by sensing circuitry. The ECAP information may include digitized portions or all of the ECAP signal, filtered portions of the ECAP signal, or raw data representative of the sensed ECAP signal that can be processed by the processing circuitry. The processing circuitry may determine, based on the ECAP information, that the ECAP signal includes at least one of an N2 peak, P3 peak, or N3 peak. These peaks may be latter occurring in the ECAP signal than a P2 and N1 peak. Other latter occurring peaks after the N3 peak may be detected in other examples. The processing circuitry may then control delivery of electrical stimulation based on at least one of the N2 peak, P3 peak, or N3 peak.

In some examples, the processing circuitry is configured to select at least one of the N2 peak, P3 peak, or N3 peak based on temporal proximity of a stimulus artifact in the ECAP signal to at least one of the N2 peak, P3 peak, or N3 peak. For example, if the stimulus artifact occurs within a threshold time of the N1 or P2 peak, the processing circuitry will look to the presence of at least one of the N2 peak, P3 peak, or N3 peak. The processing circuitry may then select one or more of the N2 peak, P3 peak, or N3 peak that occurs more than a threshold time from the stimulation artifact. This process may reduce the impact of the stimulation artifact on the ECAP signal features.

In some examples, the processing circuitry is configured to select at least one of the N2 peak, P3 peak, or N3 peak based on a pulse width of a stimulation pulse that elicited the ECAP signal. For example, longer pulse widths may interfere with earlier occurring peaks in the ECAP signal. The processing circuitry may thus select latter occurring N2, P3, N3, or other peaks in the ECAP signal for longer pulse widths of the stimulation pulse to reduce any impact of the stimulation artifact on detection of selected features of the ECAP signal. The processing circuitry may determine a characteristic value of the ECAP signal based on at least one of the N2 peak, P3 peak, or N3 peak. Although a longer pulse width may encumber the N1 peak, the P2 peak may be relatively unaffected in some examples because it still occurs late enough in the ECAP signal. In one example, the processing circuitry is configured to determine the characteristic value as an amplitude between a P2 peak of the ECAP signal and the N2 peak. The amplitude between two peaks refers to the total magnitude (e.g., voltage magnitude) that separates each peak. In another example, the processing circuitry is configured to determine the characteristic value as an amplitude between the N2 peak and the P3 peak. In another example, the processing circuitry is configured to determine the characteristic value as an amplitude between the P3 peak and the N3 peak. Peaks that occur later than the N3 peak (e.g., P4, N4, etc.) may be used to determine the characteristic value in other examples if they are detectable in the sensed ECAP signal. In some examples, processing circuitry may determine the characteristic value according to total, average, weighted average, or other combinations of two or more pairs of peaks or multiple peaks as measured from a zero baseline.

System 100 may select one or more values of a parameter that defines subsequent stimulation pulses according to one or more characteristic values calculated from a sensed ECAP signal. For example, processing circuitry may be configured to determine a difference between the characteristic value of the ECAP signal and a target ECAP characteristic value. The target ECAP characteristic value may be a target ECAP characteristic value that indicates appropriate stimulation intensity for the patient. The processing circuitry can then calculate, based on the difference, at least one parameter value that at least partially defines the electrical stimulation. The processing circuitry can then control delivery of the electrical stimulation to patient 105 according to the at least one parameter value that was determined from the characteristic value of the ECAP signal. For example, the processing circuitry may control stimulation circuitry of IMD 110 to deliver the electrical stimulation. The processing circuitry may continue this process such that the characteristic values of the ECAP signals are feedback into a closed-loop policy that controls one or more parameters of electrical stimulation.

Although in one example IMD 110 takes the form of an SCS device, in other examples, IMD 110 takes the form of any combination of deep brain stimulation (DBS) devices, implantable cardioverter defibrillators (ICDs), pacemakers, cardiac resynchronization therapy devices (CRT-Ds), left ventricular assist devices (LVADs), implantable sensors, orthopedic devices, or drug pumps, as examples. Moreover, techniques of this disclosure may be used to determine stimulation thresholds (e.g., perception thresholds and detection thresholds) associated any one of the aforementioned IMDs and then use a stimulation threshold to inform the intensity (e.g., stimulation levels) of therapy.

Figure 2:
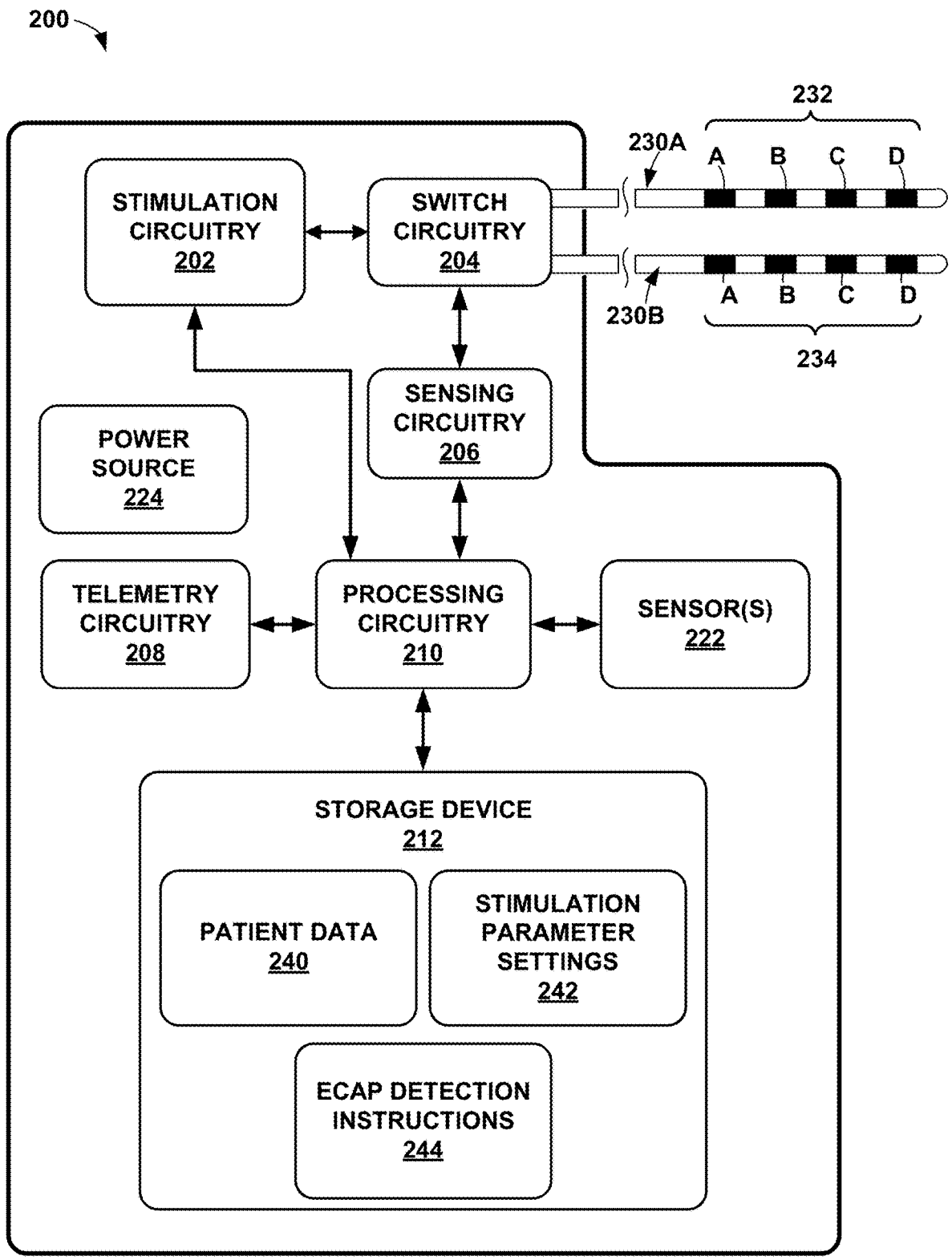
FIG. 2 is a block diagram illustrating an example configuration of components of an IMD, in accordance with one or more techniques of this disclosure.

FIG. 2 is a block diagram illustrating an example configuration of components of an IMD 200, in accordance with one or more techniques of this disclosure. IMD 200 may be an example of IMD 110 of FIG. 1. In the example shown in FIG. 2, IMD 200 includes stimulation generation circuitry 202, switch circuitry 204, sensing circuitry 206, telemetry circuitry 208, processing circuitry 210, storage device 212, sensor(s) 222, and power source 224.

In the example shown in FIG. 2, storage device 212 stores patient data 240, stimulation parameter settings 242, and ECAP detection instructions 244 in separate memories within storage device 212 or separate areas within storage device 212. Patient data 240 may include parameter values, target characteristic values, or other information specific to the patient. In some examples, stimulation parameter settings 242 may include stimulation parameter values for respective different stimulation programs selectable by the clinician or patient for therapy. In this manner, each stored therapy stimulation program, or set of stimulation parameter values, of stimulation parameter settings 242 defines values for a set of electrical stimulation parameters (e.g., a stimulation parameter set), such as a stimulation electrode combination, electrode polarity, current or voltage amplitude, pulse width, pulse rate, and pulse shape. Storage device 212 may also store ECAP detection instructions 244 that defines values for a set of electrical stimulation parameters (e.g., a control stimulation parameter set) configured to elicit a detectable ECAP signal, such as a stimulation electrode combination, electrode polarity, current or voltage amplitude, pulse width, pulse rate, and pulse shape. ECAP detection instructions 244 may also have additional information such as instructions regarding when to deliver control pulses based on the pulse width and/or frequency of the informed pulses defined in stimulation parameter settings 242, detection windows for detecting ECAP signals, instructions for determining characteristic values from ECAP signals, etc. For example, ECAP detection instructions 244 may define that characteristic values of ECAP signals are to be determined based on which peaks are present in the ECAP signal, encroachment of stimulation artifact on one or more peaks, or desired pulse widths of stimulation, as described herein.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or directed sensed signals from one or more of electrodes 232, 234 to sensing circuitry 206. In other examples, stimulation generation circuitry 202 and/or sensing circuitry 206 may include sensing circuitry to direct signals to and/or from one or more of electrodes 232, 234, which may or may not also include switch circuitry 204.

Sensing circuitry 206 is configured to monitor signals from any combination of electrodes 232, 234. In some examples, sensing circuitry 206 includes one or more amplifiers, filters, and analog-to-digital converters. Sensing circuitry 206 may be used to sense physiological signals, such as ECAP signals. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Telemetry circuitry 208 supports wireless communication between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via telemetry circuitry 208. Processing circuitry 210 may store updates to the stimulation parameter settings 242 or any other data in storage device 212. Telemetry circuitry 208 in IMD 200, as well as telemetry circuits in other devices and systems described herein, such as the external programmer, may accomplish communication by radiofrequency (RF) communication techniques. In addition, telemetry circuitry 208 may communicate with an external medical device programmer (not shown in FIG. 2) via proximal inductive interaction of IMD 200 with the external programmer. The external programmer may be one example of external programmer 150 of FIG. 1. Accordingly, telemetry circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to stimulation parameter settings 242 and any other instructions stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 210 also controls stimulation generation circuitry 202 to generate and apply the stimulation signals to selected combinations of electrodes 232, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques. In some examples, one or more of electrodes 232 and 234 are suitable for sensing the ECAPs. For instance, electrodes 232 and 234 may sense the voltage amplitude of a portion of the ECAP signals, where the sensed voltage amplitude, such as the voltage difference between features within the signal, is a characteristic the ECAP signal.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. As discussed above, storage device 212 is configured to store patient data 240, stimulation parameter settings 242, and ECAP detection instructions 244.

In some examples, storage device 212 may store instructions on how processing circuitry 210 can adjust stimulation pulses in response to the determined characteristic values of ECAP signals. For example, processing circuitry 210 may monitor ECAP characteristic values obtained from ECAP signals (or a signal derived from the ECAP signal) to modulate stimulation parameter values (e.g., increase or decrease stimulation intensity to maintain a target therapeutic effect). In some examples, a target ECAP characteristic value may vary for different situations for a patient, such as different posture states, times of day, activities, etc.

Sensor(s) 222 may include one or more sensing elements that sense values of a respective patient parameter, such as posture state. As described, electrodes 232 and 234 may be the electrodes that sense the characteristic value of the ECAP signal. Sensor(s) 222 may include one or more accelerometers, optical sensors, chemical sensors, temperature sensors, pressure sensors, or any other types of sensors. Sensor(s) 222 may output patient parameter values that may be used as feedback to control delivery of therapy. For example, sensor(s) 222 may indicate patient activity, and processing circuitry 210 may increase the frequency of control pulses and ECAP sensing in response to detecting increased patient activity. In one example, processing circuitry 210 may initiate control pulses and corresponding ECAP sensing in response to a signal from sensor(s) 222 indicating that patient activity has exceeded an activity threshold. Conversely, processing circuitry 210 may decrease the frequency of control pulses and ECAP sensing in response to detecting decreased patient activity. For example, in response to sensor(s) 222 no longer indicating that the sensed patient activity exceeds a threshold, processing circuitry 210 may suspend or stop delivery of control pulses and ECAP sensing. In this manner, processing circuitry 210 may dynamically deliver control pulses and sense ECAP signals based on patient activity to reduce power consumption of the system when the electrode-to-neuron distance is not likely to change and increase system response to ECAP changes when electrode-to-neuron distance is likely to change. IMD 200 may include additional sensors within the housing of IMD 200 and/or coupled via one of leads 130 or other leads. In addition, IMD 200 may receive sensor signals wirelessly from remote sensors via telemetry circuitry 208, for example. In some examples, one or more of these remote sensors may be external to patient (e.g., carried on the external surface of the skin, attached to clothing, or otherwise positioned external to patient 105). In some examples, signals from sensor(s) 222 indicate a position or body state (e.g., sleeping, awake, sitting, standing, or the like), and processing circuitry 210 may select target ECAP characteristic values according to the indicated position or body state.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

Figure 3:
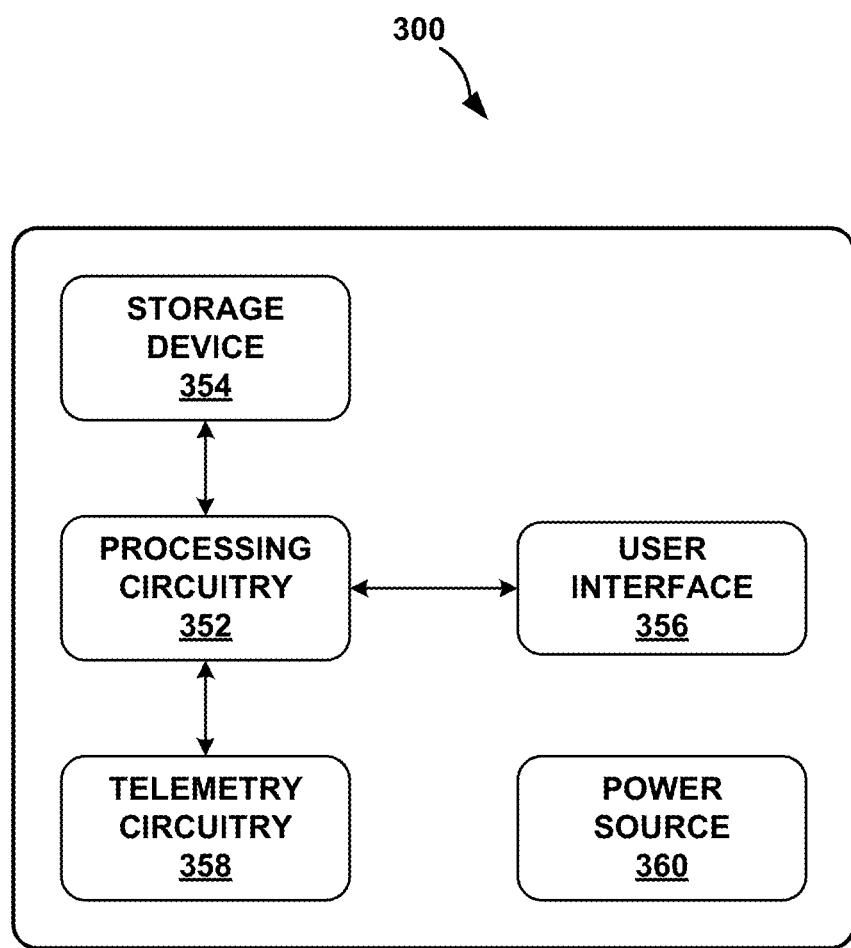
FIG. 3 is a block diagram illustrating an example configuration of components of an example external programmer, in accordance with one or more techniques of this disclosure.

FIG. 3 is a block diagram illustrating an example configuration of components of an example external programmer 300. External programmer 300 may be an example of external programmer 150 of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, telemetry circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory, select a spatial electrode pattern, or receive a user input and send a corresponding command to IMD 200, or instructions for any other functionality. In addition, storage device 354 may include a plurality of programs, where each program includes a parameter set that defines therapy stimulation or control stimulation. Storage device 354 may also store data received from a medical device (e.g., IMD 110). For example, storage device 354 may store ECAP related data recorded at a sensing module of the medical device, and storage device 354 may also store data from one or more sensors of the medical device.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation, identified posture states, sensed patient parameter values, or any other such information. User interface 356 may also receive user input (e.g., indication of when the patient perceives a stimulation pulse) via user interface 356. The input may be, for example, in the form of pressing a button on a keypad or selecting an icon from a touch screen. The input may request starting or stopping electrical stimulation, the input may request a new spatial electrode pattern or a change to an existing spatial electrode pattern, of the input may request some other change to the delivery of electrical stimulation.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameter values to IMD 110 for delivery of electrical stimulation therapy. Although IMD 110 may determine characteristic values for ECAP signals and control the adjustment of stimulation parameter values in some examples, programmer 300 may perform these tasks alone or together with IMD 110 in a distributed function.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external programmer 300 provides visual, audible, and/or tactile notifications that indicate there are new instructions. External programmer 300 requires receiving user input acknowledging that the instructions have been completed in some examples.

User interface 356 of external programmer 300 may also be configured to receive an indication from a clinician instructing a processor of the medical device to update one or more therapy stimulation programs or to update the target characteristic values for ECAP signals. Updating therapy stimulation programs and target characteristic values may include changing one or more parameters of the stimulation pulses delivered by the medical device according to the programs, such as amplitude, pulse width, frequency, and pulse shape of the informed pulses and/or control pulses. User interface 356 may also receive instructions from the clinician commanding any electrical stimulation, including therapy stimulation and control stimulation to commence or to cease. In some examples, user interface 356 may receive user selection of pulse widths or other stimulation parameter values that define stimulation and/or affect which features of ECAP signals are selected by programmer 300 or IMD 200. In other examples, user interface 356 may present selectable options, and receive input, for which features of an ECAP signal should be used to determine the characteristic values of ECAP signals.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
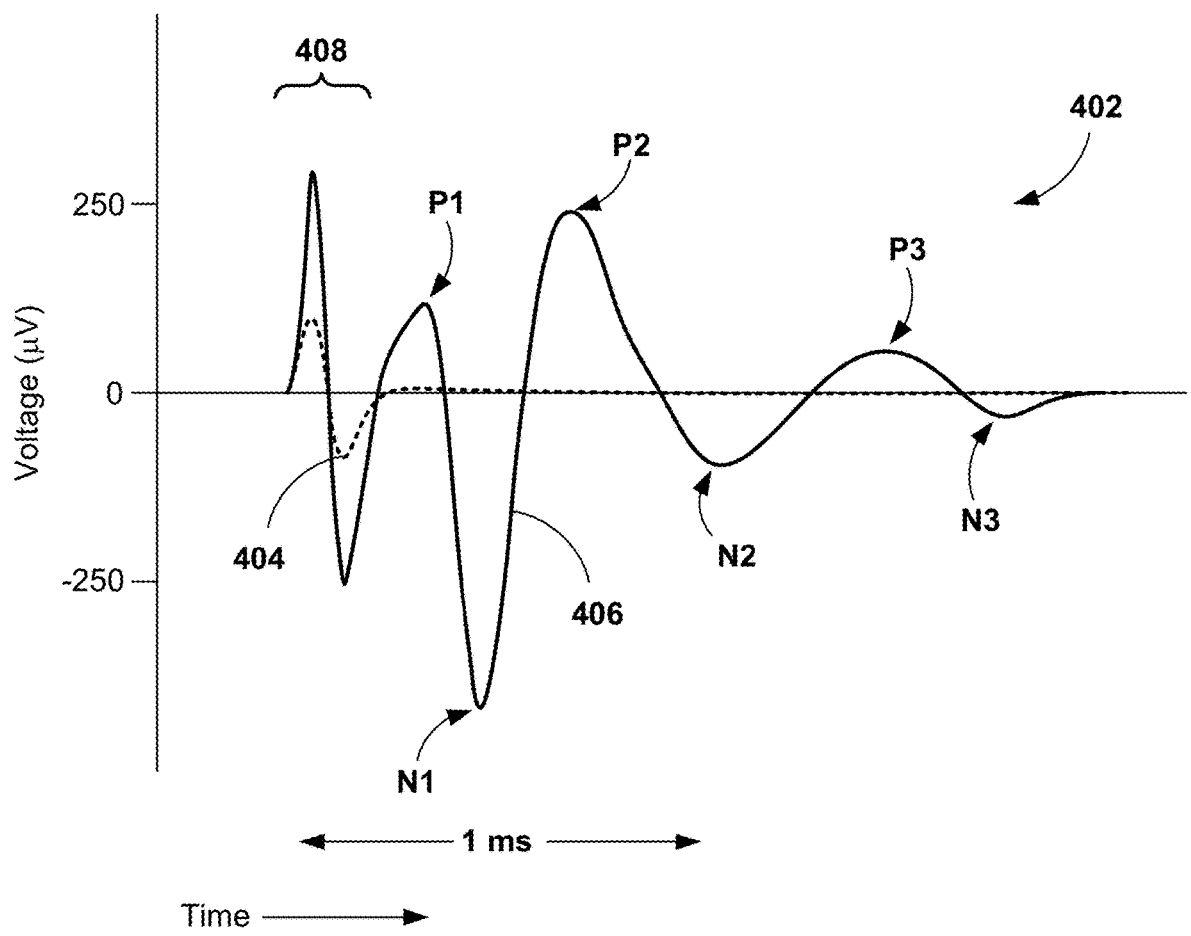
FIG. 4 is a graph of example evoked compound action potentials (ECAPs) sensed for respective stimulation pulses, in accordance with one or more techniques of this disclosure.

FIG. 4 is a graph 402 of example evoked compound action potentials (ECAPs) sensed for respective stimulation pulses, in accordance with one or more techniques of this disclosure. As shown in FIG. 4, graph 402 shows example ECAP signal 404 (dotted line) and ECAP signal 406 (solid line). In some examples, each of ECAP signals 404 and 406 are sensed from stimulation pulses that were delivered from a guarded cathode, where the control pulses are bi-phasic pulses including an interphase interval between each positive and negative phase of the pulse. In some such examples, the guarded cathode includes stimulation electrodes located at the end of an 8-electrode lead (e.g., leads 130 of FIG. 1) while two sensing electrodes are provided at the other end of the 8-electrode lead. ECAP signal 404 illustrates the voltage amplitude sensed as a result from a sub-detection threshold stimulation pulse. In other words, the stimulation pulse did not elicit a detectable ECAP signal in ECAP signal 404. Peaks 408 of ECAP signal 404 are detected and represent the artifact of the delivered stimulation pulse (e.g., a control pulse that may or may not contribute to a therapeutic effect for the patient). However, no propagating signal is detected after the artifact in ECAP signal 404 because the stimulation pulse was sub-detection threshold (e.g., the intensity of the stimulation pulse was insufficient to cause nerve fibers to depolarize and generate a detectable ECAP signal).

In contrast to ECAP signal 404, ECAP signal 406 represents the voltage amplitude detected from a supra-detection threshold stimulation pulse. Peaks 408 of ECAP signal 406 are detected and represent the artifact of the delivered stimulation pulse. After peaks 408, ECAP signal 406 also includes peaks P1, N1, P2, N2, P3, and N3 which are example features (e.g., peaks) representative of propagating action potentials from an ECAP. The example duration of the artifact and peaks P1, N1, and P2 is approximately 1 millisecond (ms), and latter occurring peaks (e.g., N2, P3, and N3) may take longer to develop. In some examples, latter occurring peaks may not be detectable in all patients or for relatively shorter pulse widths. In some instances, additional peaks not shown may occur. The time between two points in the ECAP signal may be referred to as a latency of the ECAP and may indicate the types of fibers being captured by the control pulse. ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Other characteristics of the ECAP signal may be used in other examples.

The amplitude of the ECAP signal (e.g., some or all peaks within the ECAP signal) generally increases with increased amplitude of the stimulation pulse, as long as the pulse amplitude is greater than threshold such that nerves depolarize and propagate the signal. The target ECAP characteristic (e.g., the target ECAP amplitude) may be determined from the ECAP signal detected from a control pulse when informed pulses are determined to deliver effective therapy to patient 105. The ECAP signal thus is representative of the distance between the stimulation electrodes and the nerves appropriate for the stimulation parameter values of the informed pulses delivered at that time.

Figure 5A:
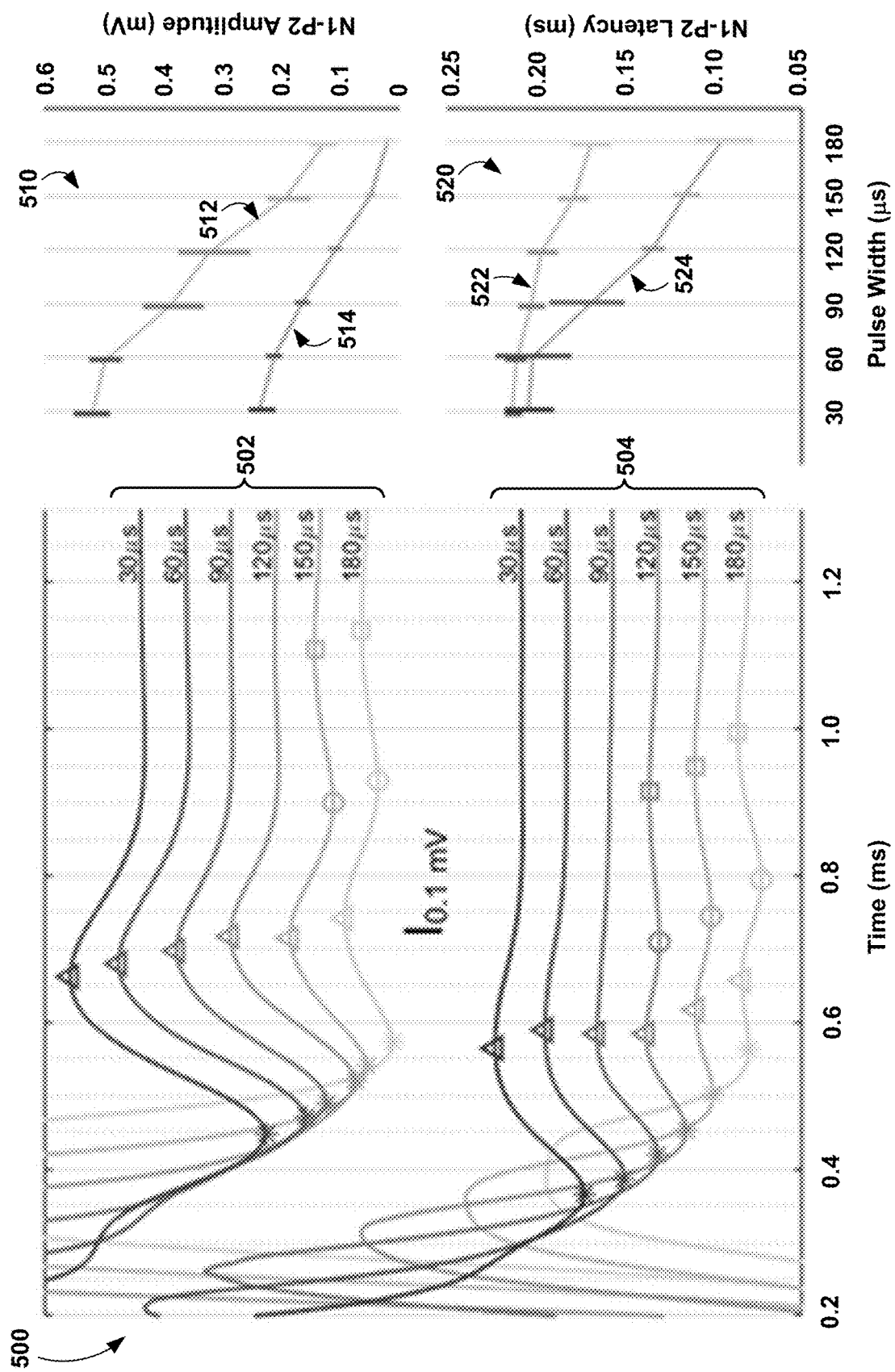
FIG. 5A includes graphs of example ECAP signals and respective features for different subjects, in accordance with one or more techniques of this disclosure.

FIG. 5A includes graphs of example ECAP signals and respective features for different subjects, in accordance with one or more techniques of this disclosure. As shown in the example graph 500 of FIG. 5A, different stimulation pulses were delivered at different pulse widths for two different sheep subjects, which elicited respective ECAP signals. ECAP signals 502 correspond to a first sheep, and ECAP signals 504 correspond to a second sheep. The delivered stimulation pulses were produced by percutaneous 1×8 spinal cord stimulation leads located in the epidural space at T8. Balanced biphasic stimulation pules were delivered with a constant charge of 75 nC/phase on electrode 6 (E6) with respect to electrode 7 (E7). Averaged differential recordings of the biopotentials—that is the stimulation artifact and the ECAP generated from the neurostimulation were recorded on E2/E1 from the same lead. These are just example parameters for these subjects, as other example parameter values may be used in other examples.

For graphs 500, 510, and 520, averaged ECAP recordings in sheep with swept pulse width stimulation, along with graphs (median and 10th-90th percentile ranges) of N1-P2 amplitude (plot 510) and N1-P2 latency (separation) (plot 520) as a function of pulse width. Example cathodic phases had a duration of 30 microsecond (μs), 60 μs, 90 μs, 120 μs, 150 μs, and 180 μs phase duration. Each cathodic phase had a corresponding anodic phase of similar duration and an interphase interval of 30 μs, and the combination of the cathodic phase, interphase interval, and anodic phase is referred to as the pulse width of the stimulus. In this manner, the respective pulse widths for each curve were 90 μs, 150 μs, 210 μs, 270 μs, 330 μs, and 390 μs. Symbols in graph 500 indicate location of N1 (*), P2 (Δ), N2(○), and P3(□).

ECAP signals 502 for the first sheep shows that the N1 and P2 peaks were detectable for pulse widths from 30 to 180 μs. However, N2 and P3 peaks were only detectable for the 150 μs and 180 μs pulse widths. Similarly, ECAP signals 504 for the second sheep shows that the N1 and P2 peaks were detectable for phase durations from 30 to 180 μs. However, N2 and P3 peaks were only detectable for the 120 μs, 150 μs, and 180 μs phase durations. Also evident in these recordings is a longer latency component of the ECAP signal, labeled as N2/P3, which manifests at longer pulses widths in both sheep.

Graph 510 illustrates that the N1/P2 amplitude decreased for the first sheep (line 512) and the second sheep (line 514) as pulse width increased. This is likely due to the wider pulse widths encumbering the N1 and P2 peaks. Graph 520 illustrates that the latency between the N1 and P2 peaks also decreased for the first sheep (line 522) and the second sheep (line 524) as pulse width increased. This is likely due to the wider pulse widths ending closer in time to the presence of the N1 and P2 peaks. This decline in latency indicates that latency may be used as a threshold for determining whether or not latter occurring peaks should be used for the characteristic value of the ECAP signals instead of N1 and/or P2. For example, in response to determining that the latency drops below a threshold value, IMD 200 may select peaks that occur later in the ECAP signal than N1 (and in some cases P2).

Figure 5B:
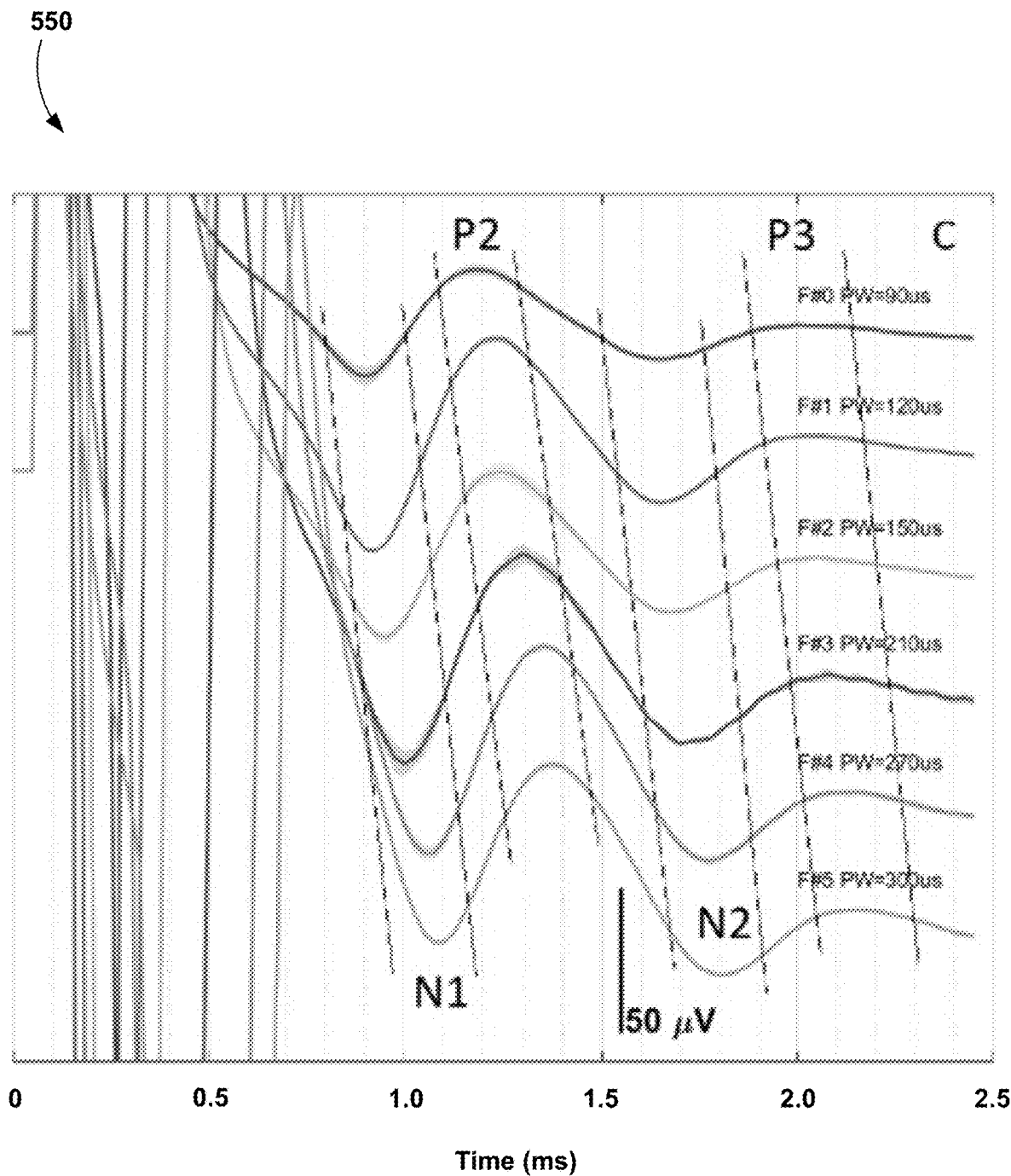
FIG. 5B is a graph of example ECAP signals and respective features of a subject, in accordance with one or more techniques of this disclosure.

FIG. 5B is a graph 550 of example ECAP signals and respective features of a subject, in accordance with one or more techniques of this disclosure. As shown in example 5B, graph 550 illustrates ECAP signals recorded from a human subject in response to delivery of different stimulation pulses having varying pulse widths of 90 μs, 120 μs, 150 μs, 210 μs, 270 μs, and 300 μs (shown in different curves from top to bottom of graph 550, respectively). The N1 and P2 peaks are present and detectable in the ECAP signals for all pulse widths. N2 and P3 peaks are also present and detectable in all of the ECAP signals. However, the amplitudes of N2 and P3 are noticeably greater at all pulse widths except for the shortest 90 μs pulse width. Therefore, the pulse width that elicits detectable, or usable, latter occurring peaks in the ECAP signal may be different for different subjects. IMD 200 or any other device may iteratively test different pulse widths in order to identify which pulse widths elicit an ECAP signal that includes detectable features of interest, such as the N2 and P3 peaks. Graph 550 also indicates that the latency is reduced between the artifact and N1 as the pulse width increases.

Figure 6:
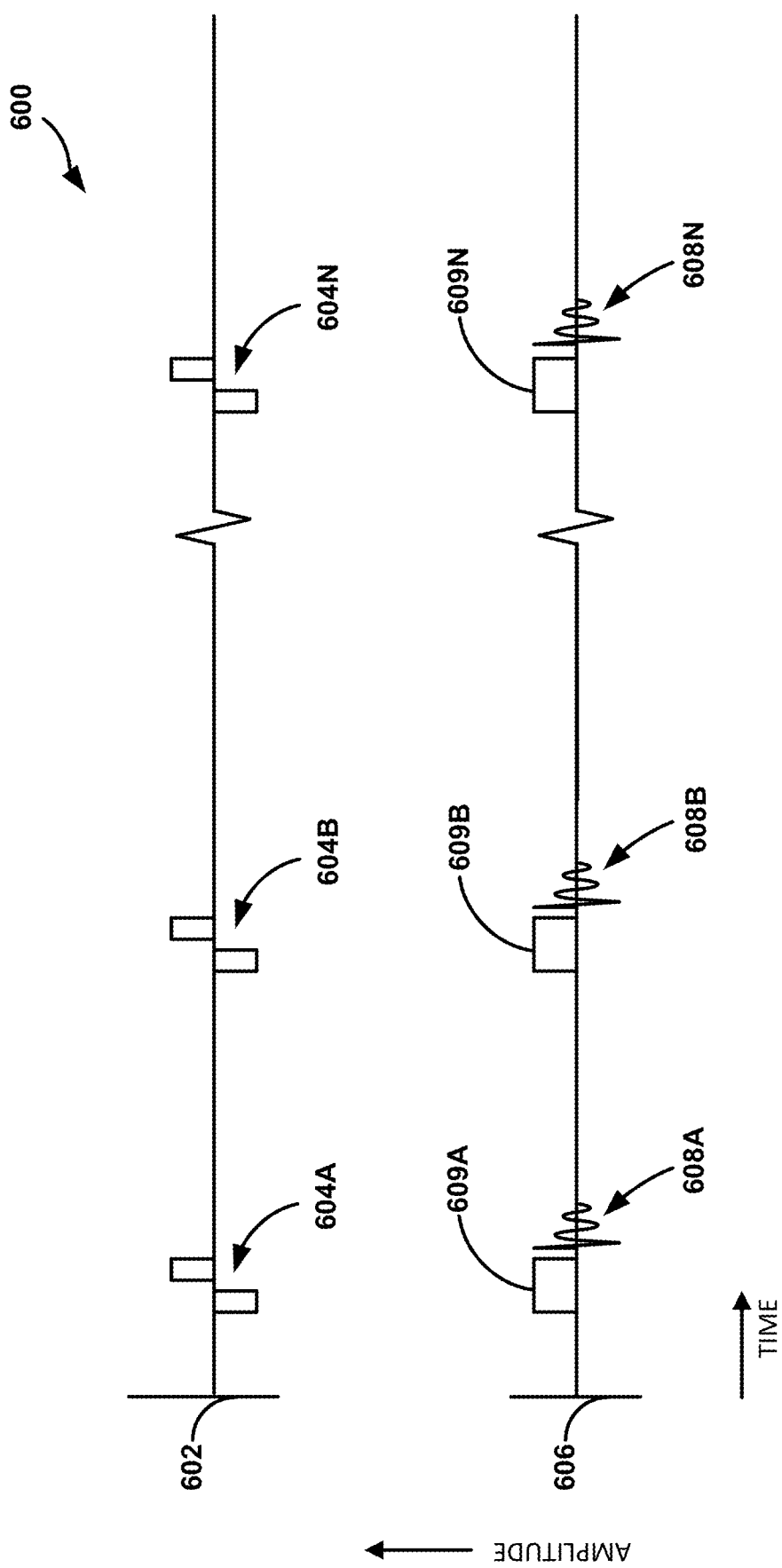
FIG. 6 is a timing diagram illustrating one example of electrical stimulation pulses and respective sensed ECAPs, in accordance with one or more techniques of this disclosure.

FIG. 6 is a timing diagram 600 illustrating one example of electrical stimulation pulses and respective sensed ECAPs, in accordance with one or more techniques of this disclosure. For convenience, FIG. 6 is described with reference to IMD 200 of FIG. 2. As illustrated, timing diagram 600 includes first channel 602, a plurality of stimulation pulses 604A-604N (collectively "stimulation pulses 604"), second channel 606, a plurality of respective ECAPs 608A-608N (collectively "ECAPs 608"), and a plurality of stimulation interference signals 609A-609N (collectively "stimulation interference signals 609"). In the example of FIG. 6, stimulation pulses 604 may be configured to contribute to therapy or not contribute to therapy. In any case, stimulation pulses 604 may elicit respective ECAPs 608 for the purpose of determining a characteristic value of the ECAPs representing a distance between electrodes and nerve fibers.

First channel 602 is a time/voltage (and/or current) graph indicating the voltage (or current) of at least one electrode of electrodes 232, 234. In one example, the stimulation electrodes of first channel 602 may be located on the opposite side of the lead as the sensing electrodes of second channel 606. Stimulation pulses 604 may be electrical pulses delivered to the spinal cord of the patient by at least one of electrodes 232, 234, and stimulation pulses 604 may be balanced biphasic square pulses with an interphase interval. In other words, each of stimulation pulses 604 are shown with a negative phase and a positive phase separated by an interphase interval. For example, a stimulation pulse 604 may have a negative voltage for the same amount of time and amplitude that it has a positive voltage. It is noted that the negative voltage phase may be before or after the positive voltage phase. Stimulation pulses 604 may be delivered according to instructions stored in storage device 212 of IMD 200.

In one example, stimulation pulses 604 may have a pulse width of less than approximately 300 microseconds (e.g., the total time of the positive phase, the negative phase, and the interphase interval is less than 300 microseconds). In another example, stimulation pulses 604 may have a pulse width of approximately 100 µs for each phase of the biphasic pulse. In some examples, the pulse width of control pulses 604 may be longer than 300 microseconds, as long as the pulse width does not interfere with the detection of the desired one or more features of the elicited ECAPs 608. As illustrated in FIG. 6, stimulation pulses 604 may be delivered via channel 602. Delivery of stimulation pulses 604 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 606 is a time/voltage (and/or current) graph indicating the voltage (or current) of at least one electrode of electrodes 232, 234. In one example, the electrodes of second channel 606 may be located on the opposite side of the lead as the electrodes of first channel 602. ECAPs 608 may be sensed at electrodes 232, 234 from the spinal cord of the patient in response to stimulation pulses 604. ECAPs 608 are electrical signals which may propagate along a nerve away from the origination of stimulation pulses 604. In one example, ECAPs 608 are sensed by different electrodes than the electrodes used to deliver stimulation pulses 604. As illustrated in FIG. 6, ECAPs 608 may be recorded on second channel 606.

Stimulation interference signals 609A, 609B, and 609N (e.g., the artifact of the stimulation pulses) may be sensed by leads 230 and may be sensed during the same period of time as the delivery of stimulation pulses 604. Since the interference signals may have a greater amplitude and intensity than ECAPs 608, any ECAPs arriving at IMD 200 during the occurrence of stimulation interference signals 609 may not be adequately sensed by sensing circuitry 206 of IMD 200. However, ECAPs 608 may be sufficiently sensed by sensing circuitry 206 because each ECAP 608, or at least a portion of ECAP 608 that includes one or more desired features of ECAP 608 that is used to detect the posture state and/or as feedback for stimulation pulses 604, falls after the completion of each a stimulation pulse 604. As illustrated in FIG. 6, stimulation interference signals 609 and ECAPs 608 may be recorded on channel 606.

Figure 7:
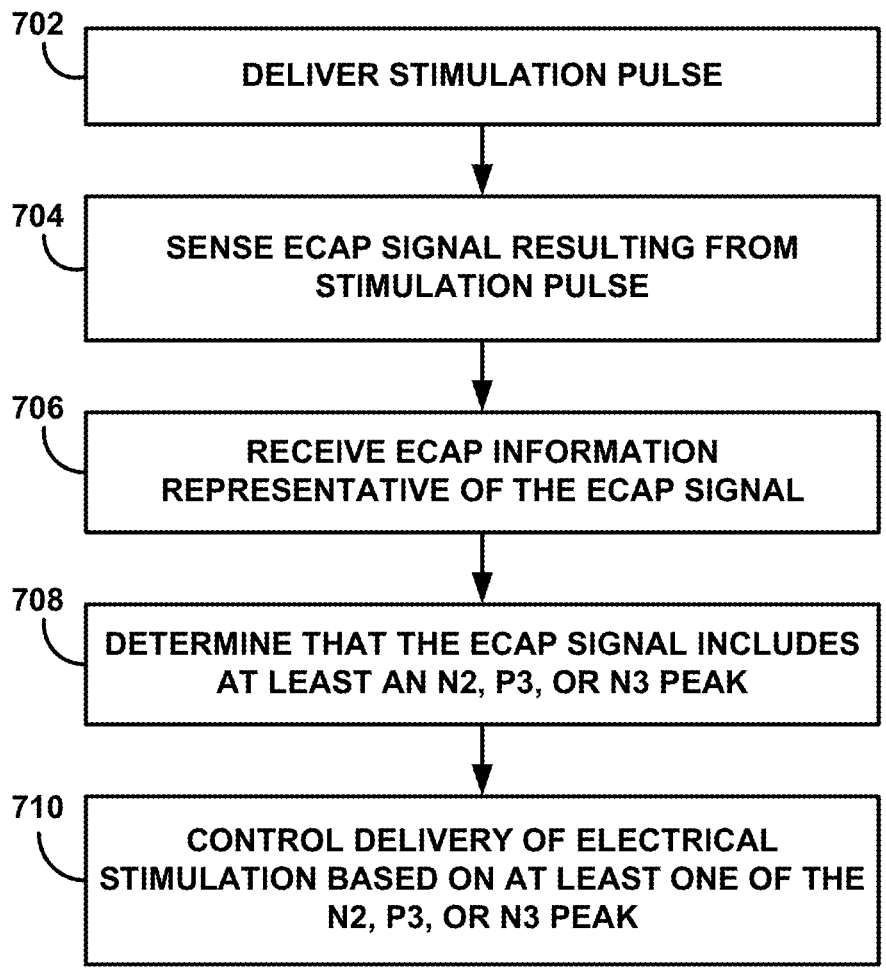
FIG. 7 is a flow diagram illustrating an example technique for controlling delivery of stimulation if certain peaks are present in an ECAP signal, in accordance with one or more techniques of this disclosure.

FIG. 7 is a flow diagram illustrating an example technique for controlling delivery of stimulation if certain peaks are present in an ECAP signal, in accordance with one or more techniques of this disclosure. IMD 200 and processing circuitry 210 will be described in the example of FIG. 7, but other IMDs such as IMD 110 or other devices or systems may perform, or partially perform, the technique of FIG. 7.

As shown in the example of FIG. 7, processing circuitry 210 controls stimulation circuitry to deliver a stimulation pulse (702). Processing circuitry 210 may also control sensing circuitry to sense an ECAP signal resulting from the delivered stimulation pulse (704). Processing circuitry 210 can then receive ECAP information from the sensing circuitry that is representative of the ECAP signal (706). For example, the ECAP information may include a filtered and digitized version of the ECAP signal.

From the ECAP information, processing circuitry 210 determines that the ECAP signal includes at least one of an N2, P3, or N3 peak (708). These peaks are latter occurring peaks than N1 or P2 peaks that may generally have larger amplitudes than the latter occurring peaks. However, N2, P3, or N3 peaks may enable wider pulse widths to be used for eliciting ECAP signals. Processing circuitry 210 can then control delivery of electrical stimulation based on at least one of the N2, P3, or N3 peaks (710). For example, processing circuitry may determine the characteristic value of ECAP signals as the amplitude between the P2/N2 peaks, N2/P3 peaks, or P3/N3 peaks. In some examples, the parameter adjusted during control may be a current amplitude or pulse width of the stimulation pulses. Processing circuitry 210 may continue to perform the process of FIG. 7 in a loop to continually use characteristic values of ECAP signals as feedback for adjusting stimulation pulses.

Processing circuitry 210 may use later occurring peaks for various reasons. For example, earlier peaks (N1 and P2) may be affected by the stimulation artifact whereas latter occurring peaks are not (or affected to a lesser extend). In other examples, short pulse width pulses may require larger amplitudes in order to deliver a charge that elicits an ECAP signal. However, the system may run out of head room to generate a sufficient amplitude at the shorter pulse width or the patient may perceive the amplitude has uncomfortable or otherwise unwanted. The system may be able to deliver pulses with longer pulse widths having a shorter amplitude because the resulting overall delivered charge is sufficient to elicit the ECAP signal. In these longer pulse width situations, later occurring peaks may be needed to detect the ECAP signal amplitude due to artifact encumbrance on earlier occurring peaks.

Figure 8:
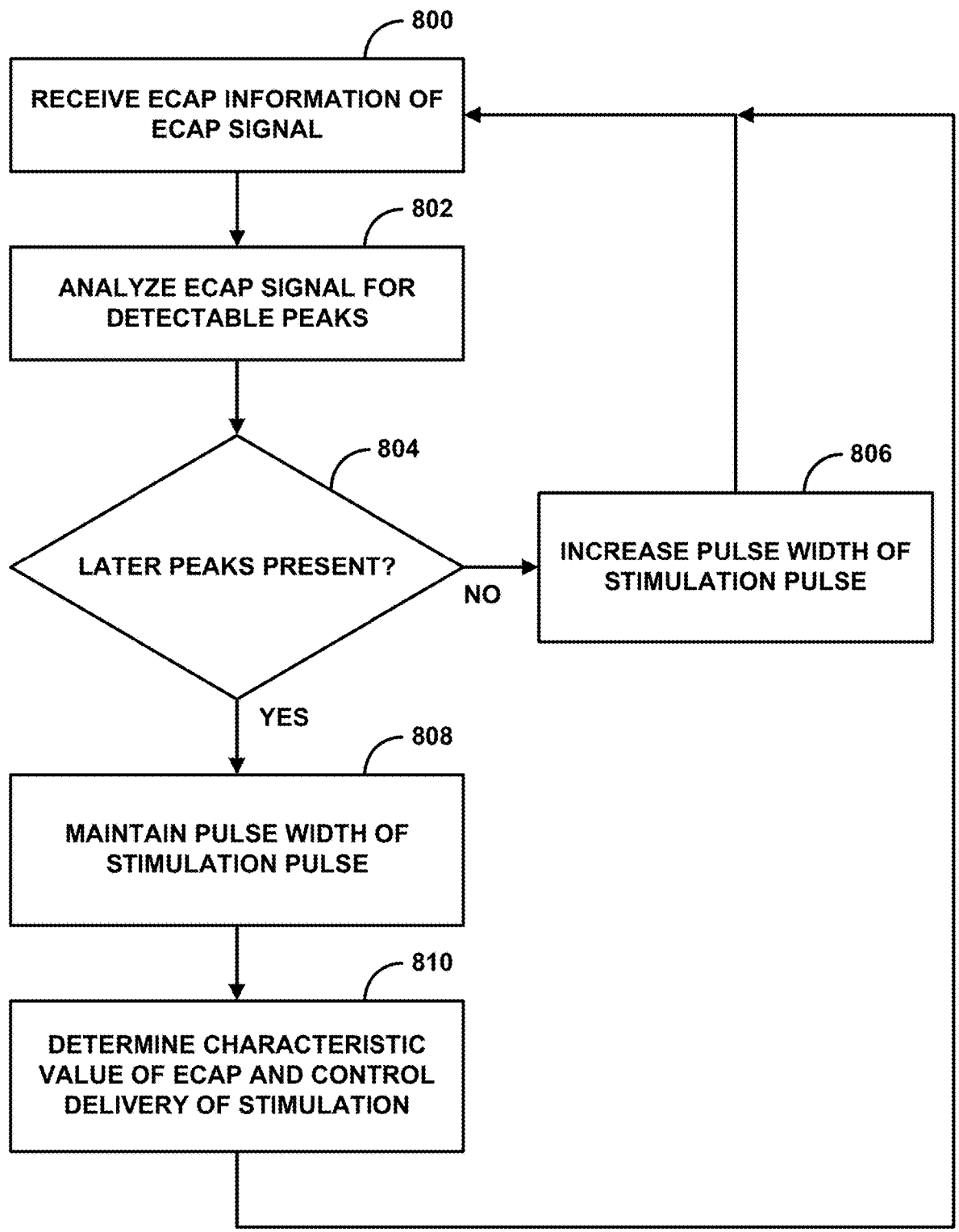
FIG. 8 is a flow diagram illustrating an example technique for adjusting pulse width of stimulation pulses until desired peaks are detected in ECAP signals, in accordance with one or more techniques of this disclosure.

FIG. 8 is a flow diagram illustrating an example technique for adjusting pulse width of stimulation pulses until desired peaks are detected in ECAP signals, in accordance with one or more techniques of this disclosure. IMD 200 and processing circuitry 210 will be described in the example of FIG. 8, but other IMDs such as IMD 110 or other devices or systems may perform, or partially perform, the technique of FIG. 8.

As shown in the example of FIG. 8, processing circuitry 210 receives ECAP information from the sensing circuitry that is representative of the ECAP signal (800). Processing circuitry 210 then analyzes the ECAP signal for detectable peaks, such as N1, P2, N2, P3, N3, etc. (802). If later occurring peaks (e.g., N2, P3, N3, etc.) are not present in the ECAP signal ("NO" branch of block 804), processing circuitry 210 increases the pulse width of the next stimulation pulse as an attempt to elicit the later occurring peaks (806). If the later occurring peaks are present in the ECAP signal ("YES" branch of block 804), processing circuitry 210 maintains the pulse width of the next stimulation pulses (808) and then determines the characteristic value of the ECAP signal and controls delivery of stimulation accordingly (810). In some examples, processing circuitry 210 may look for specific peaks to use in determining the characteristic value or look for a sufficient amplitude difference between two specific peaks that may be caused by certain pulse widths.

Alternatively, the technique of FIG. 8 may be modified to reduce the pulse width until later occurring peaks are no longer present in the ECAP signal. Processing circuitry 210 may perform such a technique in order to identify pulse widths that are short enough to elicit N1 or P2 peaks having sufficient amplitude that are no longer encumbered by the stimulation artifact. In other examples, other parameters may be changed in order to produce or remove the later occurring peaks. In some examples, processing circuitry 210 may change the shape (e.g., square, triangle, gausian, ramped) of the pulses and/or the steepness of the ramp up and/or down of the pulses in order to elicit the later occurring peaks. In some examples, processing circuitry 210 may adjust the interphase interval of a stimulation pulse in order to produce or remove the later occurring peaks. For example, processing circuitry 210 may lengthen the interphase interval between each positive and negative phase in order to elicit an ECAP signal that includes the later occurring peaks. Processing circuitry 210 may employ any one, or combination, of these parameter adjustments in order to modulate the detectable peaks in the ECAP signal.

For example, the parameter may be a current amplitude or pulse width of the stimulation pulses. Processing circuitry 210 may continue to perform the process of FIG. 8 in a loop to continually use characteristic values of ECAP signals as feedback for adjusting stimulation pulses.

Figure 9:
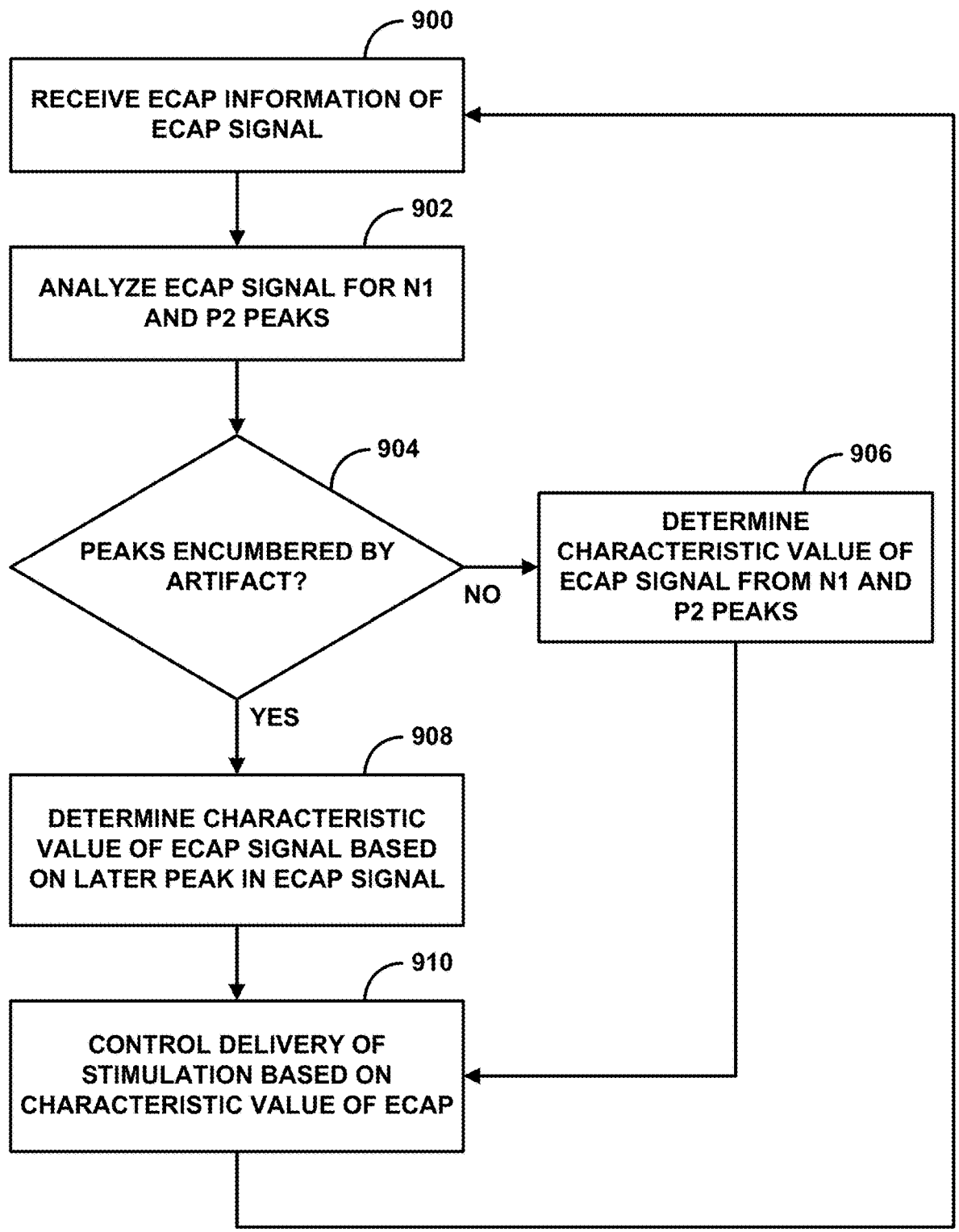
FIG. 9 is a flow diagram illustrating an example technique for determine which peaks of an ECAP signal to use as feedback for controlling electrical stimulation, in accordance with one or more techniques of this disclosure.

FIG. 9 is a flow diagram illustrating an example technique for determine which peaks of an ECAP signal to use as feedback for controlling electrical stimulation, in accordance with one or more techniques of this disclosure. IMD 200 and processing circuitry 210 will be described in the example of FIG. 9, but other IMDs such as IMD 110 or other devices or systems may perform, or partially perform, the technique of FIG. 9.

As shown in the example of FIG. 9, processing circuitry 210 receives ECAP information from the sensing circuitry that is representative of the ECAP signal (900). Processing circuitry 210 then analyzes the ECAP signal for peaks N1 and P2 (902). Processing circuitry 210 determine whether either of peaks N1 or P2 are encumbered by the stimulation artifact (904). For example, processing circuitry 210 may determine the latency, or time, from the stimulation artifact to one or both of N1 and P2 or the latency between the N1 and P2 peaks. If that latency is below a threshold time, processing circuitry 210 may determine that the stimulation artifact has encumbered or affected the amplitudes of one or both of the N1 or P2 peak. If one of N1 or P2 peaks are encumbered by the stimulation artifact ("YES" branch of block 904), processing circuitry 210 determines the characteristic value of the ECAP signal based on a later peak in the ECAP signal (e.g., N2, P3, and/or N3) (908). In some examples, processing circuitry 210 may compare the latency to multiple different threshold times that correspond to the use of different peaks that occur later in the ECAP signal. For example, processing circuitry 210 may use the earliest peaks in the ECAP signal that are associated with a threshold time that the latency did not fall below. In other words, processing circuitry 210 may select the peaks in the ECAP signal according to respective latency ranges for which the latency falls within. Generally, it may be beneficial to use the earliest occurring peaks in the ECAP signal not encumbered by the stimulation artifact because amplitudes of peaks generally decrease as the peaks occur later in time from the stimulation artifact.

If one of N1 or P2 peaks are not encumbered by the stimulation artifact ("NO" branch of block 904), processing circuitry 210 determines the characteristic value of the ECAP signal based on the N1 and P2 peaks (e.g., the amplitude difference between the N1 and P2 peaks) (906). Processing circuitry then controls delivery of stimulation based on the characteristic value of the ECAP signal (910) before receiving the next ECAP information (900).

Figure 10:
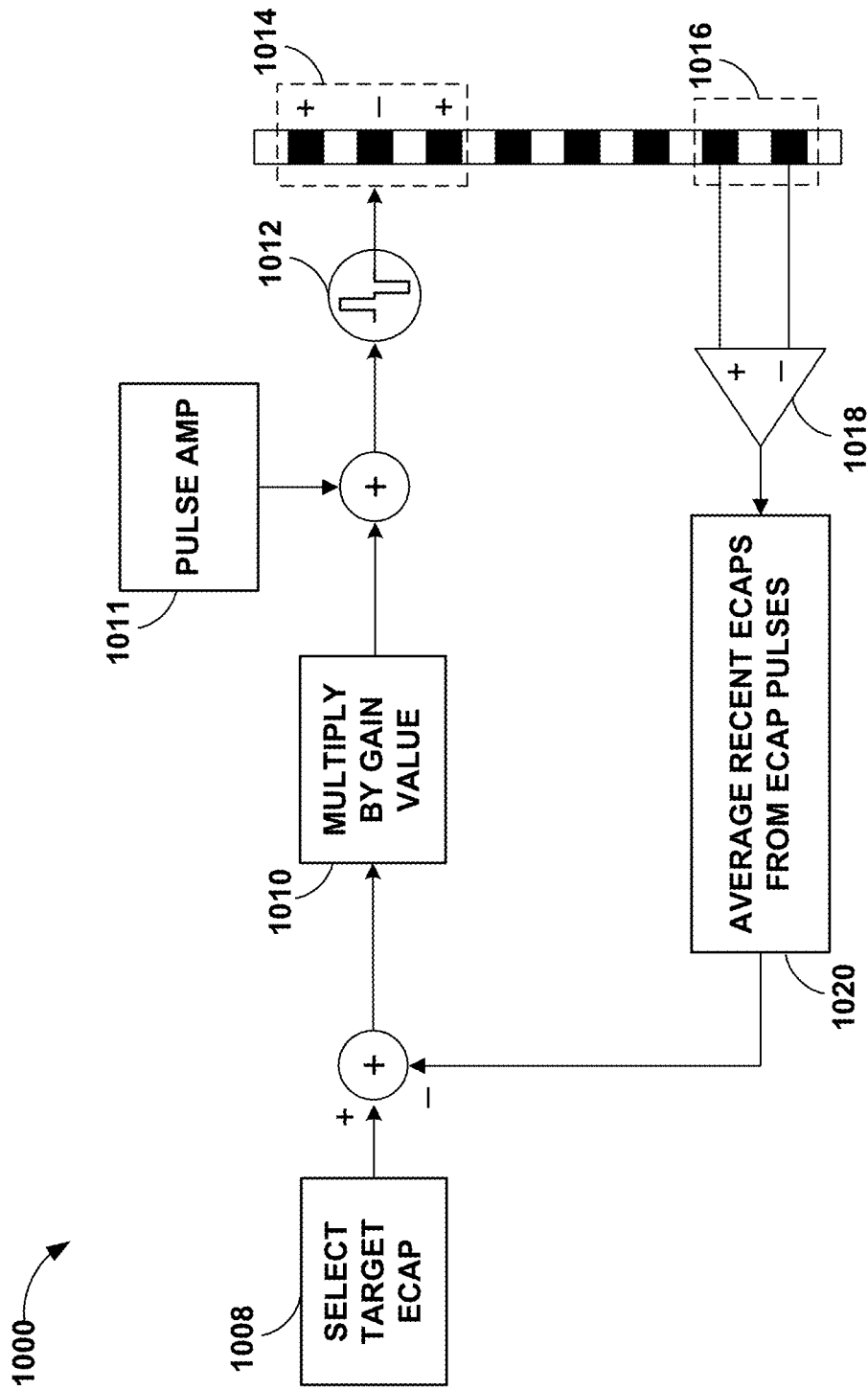
FIG. 10 is a diagram illustrating an example technique for adjusting stimulation therapy, in accordance with one or more techniques of this disclosure.

FIG. 10 is a diagram illustrating an example technique for adjusting stimulation therapy, in accordance with one or more techniques of this disclosure. As shown in the example of FIG. 10, the system, such as IMD 200 or any other device or system described herein, may dynamically adjust a parameter value that defines stimulation pulses based on a gain value representing the patient sensitivity to stimulation. Processing circuitry 210 of IMD 200 may control stimulation circuitry 202 to deliver a stimulation pulse to a patient (e.g., a control pulse from which ECAP signals can be detected and may contribute to a therapeutic effect). Processing circuitry 202 may then control sensing circuitry 206 to sense an ECAP signal elicited by the control pulse and then identify a characteristic value of the ECAP signal (e.g., an amplitude of the ECAP signal). Processing circuitry 210 may then determine, based on the characteristic of the ECAP signal and a gain value, a parameter value (e.g., an amplitude, pulse width value, pulse frequency value, and/or slew rate value) that at least partially defines another control pulse and/or an informed pulse (not shown). Processing circuitry 210 may then control stimulation circuitry 202 to deliver the next control pulse according to the determined parameter values.

As shown in FIG. 10, a control pulse 1012 is delivered to the patient via electrode combination 1014, shown as a guarded cathode of three electrodes. Control pulse 1012 may be configured to contribute to a therapeutic effect for the patient. The resulting ECAP signal is sensed by the two electrodes at the opposing end of the lead of electrode combination 1016 fed to a differential amplifier 1018. For each sensed ECAP signal, processing circuitry 210 may determine a characteristic value of the ECAP signal, such as the difference in amplitude between later occurring peaks N2 and P3 the ECAP signal. In some examples, the characteristic value may be scaled to the amplitude of delivered pulses since the values of the first derivative may not correspond in magnitude directly to amplitudes of pulses. Processing circuitry 210 may average the recently measured characteristic values 1020, such as averaging the most recent, and consecutive, 2, 3, 4, 5, 6, or more characteristic values. In some examples, the average may be a mean or median value. In some examples, one or more characteristic values may be ignored from the calculations if the characteristic value is determined to be an error. The characteristic value (or average measured characteristic value) is then subtracted from the selected target characteristic value 1008 to generate a differential value. The selected target characteristic value 1008 may be determined from an ECAP sensed when the physician or patient initially discovers effective therapy from the control pulses or informed pulses. This target characteristic value 1008 may essentially represent a reference distance between the stimulation electrodes and the target neurons (e.g., the spinal cord for the case of SCS). In some examples, processing circuitry 210 may select the target characteristic value 1008 associated with a detected posture state, to the extent the target characteristic value would change for different posture states.

The differential value is then multiplied by the gain value for the patient to generate a preliminary differential value 1010. The preliminary differential value is added to the ECAP pulse amplitude (e.g., the control pulse amplitude) to generate the new, or adjusted, ECAP pulse amplitude that at least partially defines the next control pulse 1012. In some examples, processing circuitry 210 may adjust informed pulses, in addition to control pulses, when the informed pulses to not elicit detectable ECAP signals. For example, to adjust the informed pulse amplitude, the differential value that was created after multiplication by the gain value 1010 is multiplied by a scaling factor to generate a therapy differential value. For example, the scaling factor may be the ratio of the previously delivered informed pulse amplitude to the previously delivered control pulse amplitude. The therapy differential value is then added to the previously delivered informed pulse amplitude to generate the new, or adjusted, informed pulse amplitude that at least partially defines the next informed pulse. This process can be applied to the informed pulses from multiple stimulation programs. For example, if informed pulses from two different stimulation programs are delivered as a part of stimulation therapy, the system may multiply the respective scaling factors by the differential value to obtain a respective therapy differential value for the informed pulses of each stimulation program. The next informed pulse (or pulses if multiple stimulation programs are involved in therapy) is then delivered, interleaved with the control pulse 1012, to the patient via electrode combination 1014 or a different set of electrodes in other examples. In some examples, at least two control pulses may be delivered, and at least two respective ECAP signals sensed, between consecutive informed pulses. This increased frequency of control pulses may allow the system to quickly adjust informed pulse amplitudes for any changes in the distance between electrodes and neurons.

Although the technique of FIG. 10 is described for adjusting the amplitude of the control pulses, other parameter values may be changed in other examples. For example, sensed ECAP signals may be used to increase or decrease the pulse width of the control pulse to adjust the amount of charge delivered to the tissue to maintain consistent volume of neural activation. In other examples, electrode combinations may be adjusted in order to deliver different amounts of charge and modify the number of neurons being recruited by each informed pulse. In other examples, processing circuitry 210 may be configured to adjust the slew rate of the control pulses (i.e., the rate of change of the voltage and/or amplitude at the beginning and/or end of the pulse or each phase of the pulse) in response to a characteristic of the ECAP signal, such as the amplitude of recent ECAP amplitudes.

Figure 11:
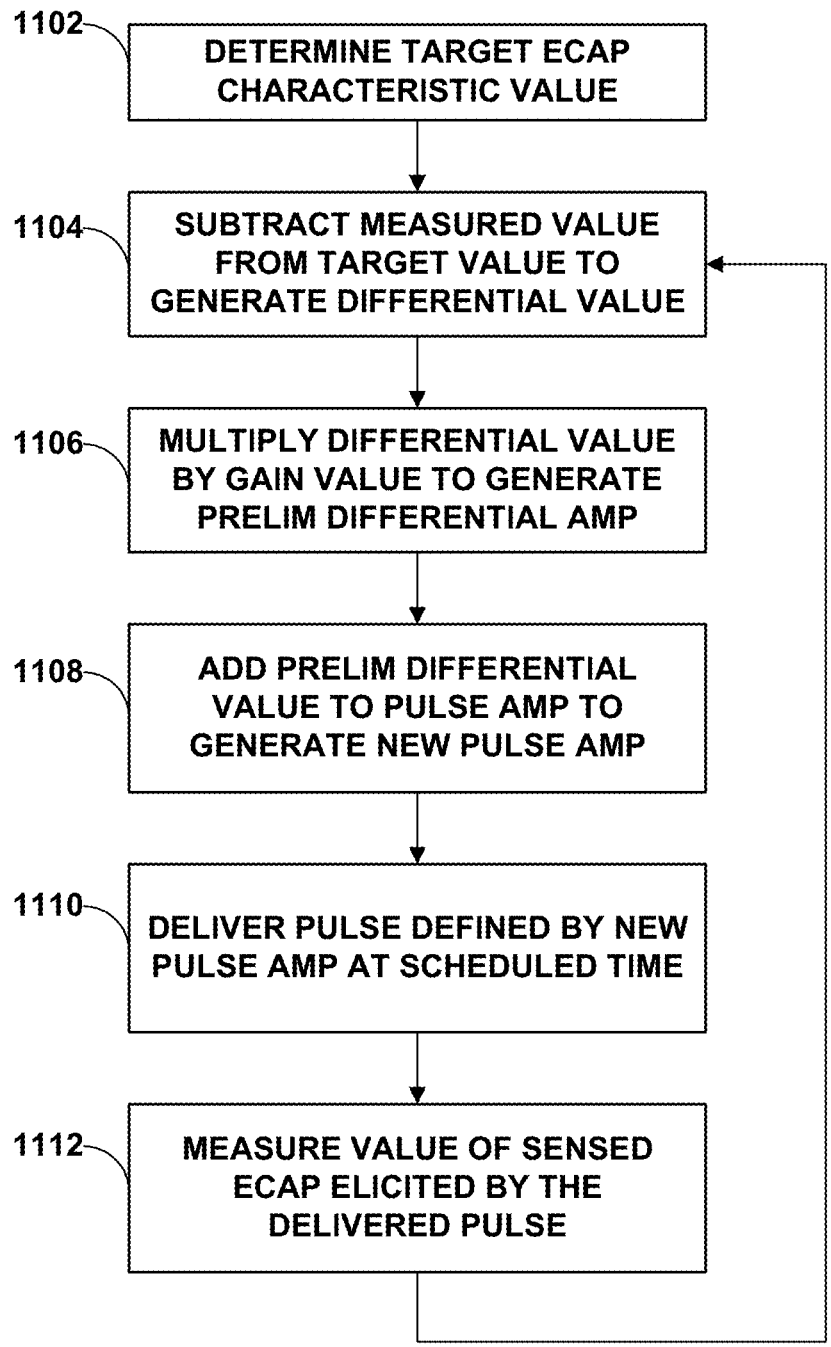
FIG. 11 is a flow diagram illustrating the example technique for adjusting stimulation therapy as shown in the diagram of FIG. 10.

FIG. 11 is a flow diagram illustrating the example technique for adjusting stimulation therapy as shown in the diagram of FIG. 10. IMD 200 and processing circuitry 210 will be described in the example of FIG. 11, but other IMDs such as IMD 110 or other devices or systems may perform, or partially perform, the technique of FIG. 11.

In the example of FIG. 11, processing circuitry 210 determines the target ECAP amplitude (1102). The target characteristic value may be determined based on sample stimulation initially delivered to the patient. The target characteristic value may be difference between the maximum and minimum values of the first derivative, for example, but other measures of ECAP amplitude may be used instead. In some examples, processing circuitry 210 is configured to automatically change the target characteristic value over a period of time according to a predetermined function (e.g., a sinusoid function) in order to change the volume of neuron activation and, in some examples, the perceived sensation of the informed pulses.

Processing circuitry 210 receives a measured characteristic value from the previously sensed ECAP signal. In order to use the ECAP signal as feedback to control the next stimulation pulses of electrical stimulation therapy for the patient, processing circuitry 210 subtracts the measured characteristic value from the target characteristic value to generate a differential value (1104). In some examples, or as additional measured characteristic value are available from the process, processing circuitry 210 may average a certain number of recent measured characteristic values (e.g., two or more) to create a rolling average of measured characteristic values and subtract the average characteristic values from the target characteristic value to smooth out variations between ECAP signals. The differential value is thus a representation of how much the electrodes have moved relative to the neurons and can be used to adjust the amplitudes of the informed pulses and the control pulses to maintain consistent volume of neural activation of the neurons that provide relief to the patient.

Processing circuitry 210 then multiplies the differential value by a gain value for the patient to generate a preliminary differential value (1106). Processing circuitry 210 then uses the preliminary differential value to adjust the amplitudes of control pulses (and informed pulses if necessary). Processing circuitry 210 adds the preliminary differential value to the control pulse amplitude to generate a new control pulse amplitude (1108). Processing circuitry 210 then controls stimulation circuitry 202 to deliver a subsequent control pulse defined by the new control pulse amplitude at a scheduled time, such as according to the frequency of the control pulses or according to the next available window between informed pulses (1110). Processing circuitry 210 also controls sensing circuitry 206 to measure the amplitude of the sensed ECAP elicited by the recently delivered control pulse (1112) to use again as feedback in block 1104.

Although the technique of FIG. 11 is described for adjusting the amplitude of control pulses, a similar operation may be used to adjust other stimulation parameters in other examples. For example, parameters that contribute to the intensity of the informed pulses and control pulses may affect the volume of neural activation, such as pulse width, pulse frequency, or even pulse shape (e.g., the amount of charge per pulse). Therefore, processing circuitry 210 may adjust a different parameter instead of, or in addition to, amplitude using the sensed ECAP signal elicited from the control pulses. For example, processing circuitry 210 may increase the pulse width of the informed pulses and control pulses in response to detecting a decreased ECAP amplitude.

Figure 12:
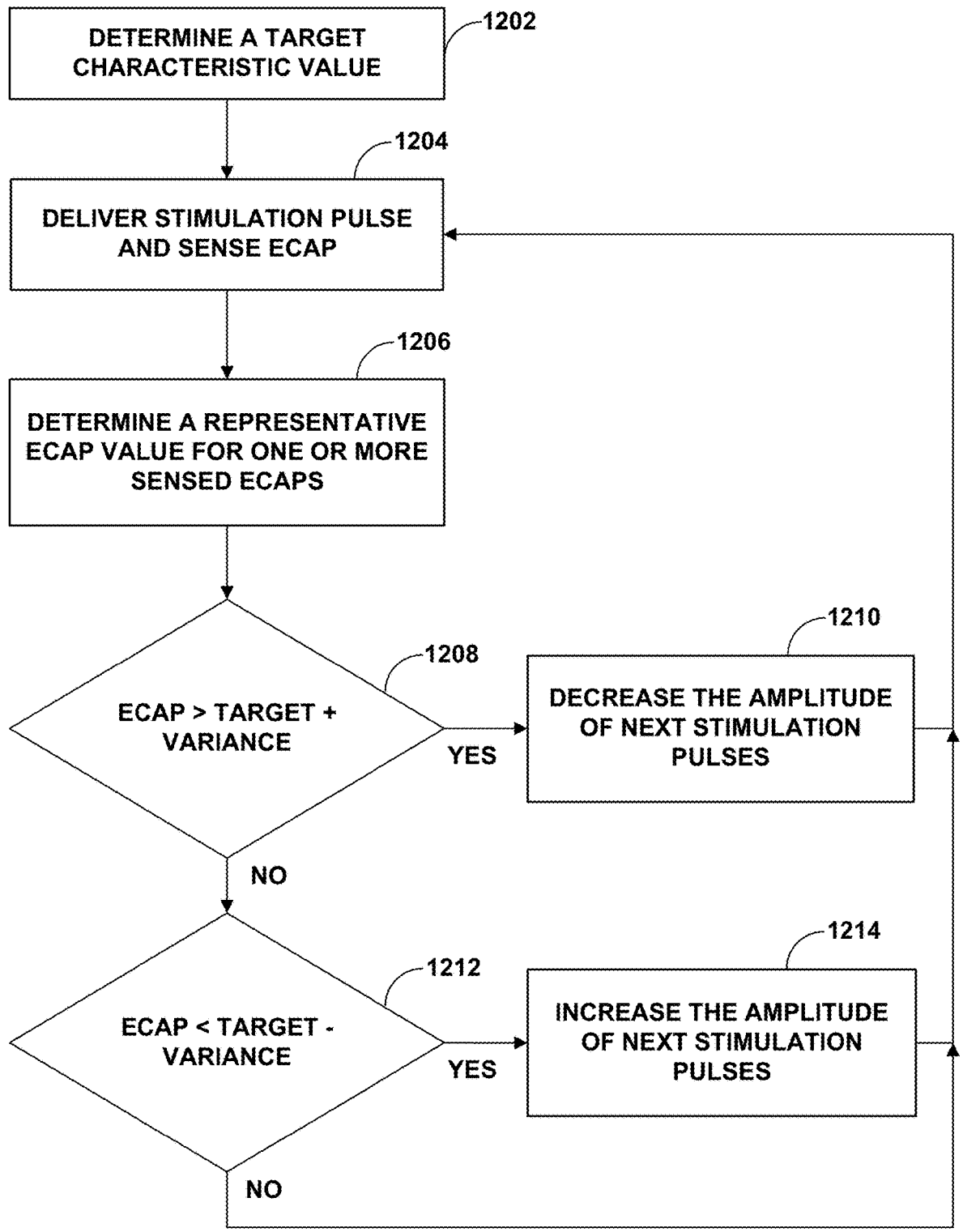
FIG. 12 is a flow diagram illustrating the example technique for adjusting stimulation therapy in accordance with one or more techniques of this disclosure.

FIG. 12 is a flow diagram illustrating the example technique for adjusting stimulation therapy in accordance with one or more techniques of this disclosure. For convenience, FIG. 12 is described with respect to IMD 200 of FIG. 2. However, the techniques of FIG. 12 may be performed by different components of IMD 200 or by additional or alternative medical devices. The technique of FIG. 12 is an example feedback mechanism for controlling stimulation therapy using sensed ECAP signals.

As illustrated in FIG. 12, processing circuitry 210 of IMD 200 may determine a target characteristic value (1202). The target characteristic value may be stored in IMD 200. One example target characteristic value may be the difference in amplitude between later occurring peaks N2 and P3 the ECAP signal. In other examples, processing circuitry 210 may automatically change the target characteristic value over a period of time according to a predetermined function (e.g., a sinusoid function, step function, exponential function, or other schedule). Processing circuitry 210 then delivers a stimulation pulse and senses the resulting ECAP elicited by the stimulation pulse (1204). Processing circuitry 210 then determines a representative characteristic value of one or more sensed ECAPs (1206). For example, the representative characteristic value may be the average amplitude of the last four sensed ECAP characteristic values. However, the representative characteristic value may be from fewer or greater ECAPs.

Processing circuitry 210 then determines if the representative characteristic value of the one or more respective ECAP is greater than the upper-bound of target ECAP adjustment window (1208). As discussed herein, the target ECAP adjustment window may be defined by the target ECAP characteristic value plus and minus a variance. Therefore, the target ECAP characteristic value plus the variance may define the upper-bound of the target ECAP adjustment window. Similarly, the target ECAP characteristic value minus the variance may define the lower-bound of the target ECAP adjustment window. In this manner, the target ECAP adjustment window may be determined so that adjustments are not made to the one or more parameters of the stimulation pulses for minor oscillations in the sensed ECAP characteristic value. If processing circuitry 210 determines that the representative amplitude of the one or more ECAPs is greater than the target ECAP characteristic value plus the adjustment window ("YES" branch of block 1208), processing circuitry 210 decreases the amplitude of the next stimulation pulses (1210). For example, the amplitudes of the stimulation pulses may be decreased by predetermined steps. As another example, the respective amplitudes of the stimulation pulses may be decreased by an amount proportional to the difference between the representative amplitude and the target ECAP characteristic value. If processing circuitry 210 determines that the representative characteristic value is less than the upper-bound of target ECAP adjustment window, ("NO" branch of block 1208), processing circuitry 210 moves to block 1212.

At block 1212, processing circuitry 210 determines if the representative characteristic value of the one or more respective ECAP is greater than the lower-bound of target ECAP adjustment window. If the representative amplitude of the one or more respective ECAP is less than the lower-bound of target ECAP adjustment window (a "YES" branch of block 1212), processing circuitry 210 increases the amplitude of the stimulation pulses by respective values (1214). For example, the amplitude of the stimulation pulse may be increased by predetermined steps. As another example, the amplitude of the stimulation pulses may be increased by an amount proportional to the difference between the representative amplitude and the target ECAP characteristic value. Processing circuitry 210 then continues to deliver a stimulation pulse according to the increased or decreased amplitudes. In some examples, the decrease or increase applied to the stimulation pulses in steps 1210 or 1214 may apply to the amplitude or other parameter of the next scheduled stimulation pulse. In this manner, even if a decrease is applied to the next stimulation pulse, the overall new amplitude of the next stimulation pulses may still be greater than the previous stimulation pulse if the scheduled amplitude of the next stimulation pulse minus the decrease is still greater than the amplitude of the previous stimulation pulse.

Although the process of FIG. 12 is described for adjusting the amplitude of the stimulation pulses (e.g., control pulses and/or stimulation pulses), other parameter values may be changed in other examples. For example, sensed ECAP signals may be used to increase or decrease the pulse width of the stimulation pulse to adjust the amount of charge delivered to the tissue to maintain consistent volume of neural activation. In other examples, electrode combinations may be adjusted in order to deliver different amounts of charge and modify the number of neurons being recruited by each informed pulse. In other examples, processing circuitry 210 may be configured to adjust the slew rate of the informed pulses (i.e., the rate of change of the voltage and/or amplitude at the beginning and/or end of the pulse or each phase of the pulse) in response to a characteristic of the ECAP signal being greater than or less than the target ECAP adjustment window. For example, if the representative characteristic value of the ECAP signal is greater than the upper-bound of the target ECAP adjustment window, processing circuitry 210 may decrease the slew rate of the next stimulation pulses (i.e., ramp up the amplitude of the pulse more slowly). If the representative amplitude of the ECAP signal is lower than the lower-bound of the target ECAP adjustment window, processing circuitry 210 may increase the slew rate of the next stimulation pulses (i.e., ramp up the amplitude of the pulse more quickly). The slew rate may contribute to the intensity of the pulse. Processing circuitry 210 may change one or more parameters defining the stimulation pulse according to the process of operation 1000.

The following examples are described herein.

Example 1: A system including processing circuitry configured to: receive evoked compound action potential (ECAP) information representative of an ECAP signal sensed by sensing circuitry; determine, based on the ECAP information, that the ECAP signal includes at least one of an N2 peak, P3 peak, or N3 peak; and control delivery of electrical stimulation based on at least one of the N2 peak, P3 peak, or N3 peak.

Example 2: The system of example 1, further including a stimulation generator configured to deliver a stimulation pulse to a patient; and the sensing circuitry configured to sense the ECAP signal elicited from the stimulation pulse.

Example 3: The system of any of examples 1 and 2, wherein the processing circuitry is configured to select at least one of the N2 peak, P3 peak, or N3 peak based on temporal proximity of a stimulus artifact in the ECAP signal to at least one of the N2 peak, P3 peak, or N3 peak.

Example 4: The system of any of examples 1 through 3, wherein the processing circuitry is configured to select at least one of the N2 peak, P3 peak, or N3 peak based on a pulse width of a stimulation pulse that elicited the ECAP signal.

Example 5: The system of any of examples 1 through 4, wherein the processing circuitry is configured to determine a characteristic value of the ECAP signal based on at least one of the N2 peak, P3 peak, or N3 peak.

Example 6: The system of example 5, wherein the processing circuitry is configured to determine the characteristic value as an amplitude between a P2 peak of the ECAP signal and the N2 peak.

Example 7: The system of any of examples 5 and 6, wherein the processing circuitry is configured to determine the characteristic value as an amplitude between the N2 peak and the P3 peak.

Example 8: The system of any of examples 5 through 7, wherein the processing circuitry is configured to determine the characteristic value as an amplitude between the P3 peak and the N3 peak.

Example 9: The system of any of examples 5 through 8, wherein the processing circuitry is configured to: determine a difference between the characteristic value of the ECAP signal and a target ECAP characteristic value; and calculate, based on the difference, at least one parameter value that at least partially defines the electrical stimulation.

Example 10: The system of example 9, wherein the processing circuitry is configured to control delivery of the electrical stimulation to a patient according to the at least one parameter value.

Example 11: The system of any of examples 1 through 10, further comprising an implantable medical device comprising the processing circuitry.

Example 12: A method including receiving, by processing circuitry, evoked compound action potential (ECAP) information representative of an ECAP signal sensed by sensing circuitry; determining, by the processing circuitry and based on the ECAP information, that the ECAP signal includes at least one of an N2 peak, P3 peak, or N3 peak; and controlling, by the processing circuitry, delivery of electrical stimulation based on at least one of the N2 peak, P3 peak, or N3 peak.

Example 13: The method of example 12, further including delivering, by a stimulation generator, a stimulation pulse to a patient; and sensing, by the sensing circuitry, the ECAP signal elicited from the stimulation pulse.

Example 14: The method of any of examples 12 and 13, further including selecting at least one of the N2 peak, P3 peak, or N3 peak based on temporal proximity of a stimulus artifact in the ECAP signal to at least one of the N2 peak, P3 peak, or N3 peak.

Example 15: The method of any of examples 12 through 14, further including selecting at least one of the N2 peak, P3 peak, or N3 peak based on a pulse width of a stimulation pulse that elicited the ECAP signal.

Example 16: The method of any of examples 12 through 15, further comprising determining a characteristic value of the ECAP signal based on at least one of the N2 peak, P3 peak, or N3 peak.

Example 17: The method of example 16, further comprising determining the characteristic value as an amplitude between a P2 peak of the ECAP signal and the N2 peak.

Example 18: The method of any of examples 16 and 17, further comprising determining the characteristic value as an amplitude between the N2 peak and the P3 peak.

Example 19: The method of any of examples 16 through 18, further comprising determining the characteristic value as an amplitude between the P3 peak and the N3 peak.

Example 20: The method of any of examples 16 through 19, further including determining a difference between the characteristic value of the ECAP signal and a target ECAP characteristic value; and calculating, based on the difference, at least one parameter value that at least partially defines the electrical stimulation.

Example 21: The method of example 20, further comprising controlling delivery of the electrical stimulation to a patient according to the at least one parameter value.

Example 22: The method of any of examples 12 through 21, wherein an implantable medical device comprises the processing circuitry.

Example 23: A computer-readable medium comprising instructions that, when executed, causes processing circuitry to receive evoked compound action potential (ECAP) information representative of an ECAP signal sensed by sensing circuitry; determine, based on the ECAP information, that the ECAP signal includes at least one of an N2 peak, P3 peak, or N3 peak; and control delivery of electrical stimulation based on at least one of the N2 peak, P3 peak, or N3 peak.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:
1. A system comprising:
processing circuitry configured to:
receive evoked compound action potential (ECAP) information representative of an ECAP signal sensed by sensing circuitry;
determine, based on the ECAP information, that the ECAP signal includes at least one of an N2 peak, P3 peak, or N3 peak;
select at least one of the N2 peak, P3 peak, or N3 peak based on temporal proximity of a stimulus artifact in the ECAP signal to at least one of the N2 peak, P3 peak, or N3 peak; and
control delivery of electrical stimulation based on the selected at least one of the N2 peak, P3 peak, or N3 peak.

2. The system of claim 1, further comprising:
a stimulation generator configured to deliver a stimulation pulse to a patient; and
the sensing circuitry configured to sense the ECAP signal elicited from the stimulation pulse.

3. The system of claim 1, wherein the processing circuitry is configured to select at least one of the N2 peak, P3 peak, or N3 peak also based on a pulse width of a stimulation pulse that elicited the ECAP signal.

4. The system of claim 1, wherein the processing circuitry is configured to determine a characteristic value of the ECAP signal based on an amplitude of the selected at least one of the N2 peak, P3 peak, or N3 peak.

5. The system of claim 4, wherein the selected at least one of the N2 peak, P3 peak, or N3 peak comprises the N2 peak, and wherein the processing circuitry is configured to determine the characteristic value as an amplitude between a P2 peak of the ECAP signal and the N2 peak.

6. The system of claim 4, wherein the selected at least one of the N2 peak, P3 peak, or N3 peak comprises the N2 peak and the P3 peak, and wherein the processing circuitry is configured to determine the characteristic value as an amplitude between the N2 peak and the P3 peak.

7. The system of claim 4, wherein the selected at least one of the N2 peak, P3 peak, or N3 peak comprises the N2 peak and the P3 peak and the N3 peak, and wherein the processing circuitry is configured to determine the characteristic value as an amplitude between the P3 peak and the N3 peak.

8. The system of claim 4, wherein the processing circuitry is configured to:
determine a difference between the characteristic value of the ECAP signal and a target ECAP characteristic value; and
calculate, based on the difference, at least one parameter value that at least partially defines the electrical stimulation.

9. The system of claim 8, wherein the processing circuitry is configured to control delivery of the electrical stimulation to a patient according to the at least one parameter value.

10. The system of claim 1, further comprising an implantable medical device comprising the processing circuitry.

11. A method comprising:
receiving, by processing circuitry, evoked compound action potential (ECAP) information representative of an ECAP signal sensed by sensing circuitry;
determining, by the processing circuitry and based on the ECAP information, that the ECAP signal includes at least one of an N2 peak, P3 peak, or N3 peak;
selecting, by the processing circuitry, at least one of the N2 peak, P3 peak, or N3 peak based on temporal proximity of a stimulus artifact in the ECAP signal to at least one of the N2 P3 peak, or N3 peak; and
controlling, by the processing circuitry, delivery of electrical stimulation based on at least one of the N2 peak, P3 peak, or N3 peak.

12. The method of claim 11, further comprising:
delivering, by a stimulation generator, a stimulation pulse to a patient; and
sensing, by the sensing circuitry, the ECAP signal elicited from the stimulation pulse.

13. The method of claim 11, further comprising selecting at least one of the N2 peak, P3 peak, or N3 peak also based on a pulse width of a stimulation pulse that elicited the ECAP signal.

14. The method of claim 11, further comprising determining a characteristic value of the ECAP signal based on an amplitude of the selected at least one of the N2 peak, P3 peak, or N3 peak.

15. The method of claim 14, wherein selecting at least one of the N2 peak, P3 peak, or N3 peak comprises selecting the N2 peak, and further comprising determining the characteristic value as an amplitude between a P2 peak of the ECAP signal and the N2 peak.

16. The method of claim 14, wherein selecting at least one of the N2 peak, P3 peak, or N3 peak comprises selecting the N2 peak and the P3 peak, and further comprising determining the characteristic value as an amplitude between the N2 peak and the P3 peak.

17. The method of claim 14, wherein selecting at least one of the N2 peak, P3 peak, or N3 peak comprises selecting the P3 peak and the N3 peak, and further comprising determining the characteristic value as an amplitude between the P3 peak and the N3 peak.

18. The method of claim 14, further comprising:
determining a difference between the characteristic value of the ECAP signal and a target ECAP characteristic value; and
calculating, based on the difference, at least one parameter value that at least partially defines the electrical stimulation.

19. The method of claim 18, further comprising controlling delivery of the electrical stimulation to a patient according to the at least one parameter value.

20. The method of claim 11, wherein an implantable medical device comprises the processing circuitry.

21. A computer-readable medium comprising instructions that, when executed, causes processing circuitry to:
receive evoked compound action potential (ECAP) information representative of an ECAP signal sensed by sensing circuitry;
determine, based on the ECAP information, that the ECAP signal includes at least one of an N2 peak, P3 peak, or N3 peak;
select at least one of the N2 peak, P3 peak, or N3 peak based on temporal proximity of a stimulus artifact in the ECAP signal to at least one of the N2 peak, P3 peak, or N3 peak; and
control delivery of electrical stimulation based on at least one of the N2 peak, P3 peak, or N3 peak.

* * * * *